(12) United States Patent
Tzou et al.

(10) Patent No.: US 12,012,442 B2
(45) Date of Patent: Jun. 18, 2024

(54) ACTIVATABLE FUSION PROTEIN AND USE THEREOF

(71) Applicant: National Yang Ming Chiao Tung University, Hsinchu (TW)

(72) Inventors: Shey-Cherng Tzou, Zhubei (TW); Yu-Yuan Hsiao, Hsinchu (TW); Fu-Yao Jiang, Xincheng Township (TW); Yan-Zhu Zhang, Hsinchu (TW); Chien-Yu Chou, Hsinchu (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 175 days.

(21) Appl. No.: 17/234,005

(22) Filed: Apr. 19, 2021

(65) Prior Publication Data
US 2022/0251169 A1 Aug. 11, 2022

(30) Foreign Application Priority Data
Feb. 3, 2021 (TW) ................ 110104031

(51) Int. Cl.
| | | |
|---|---|---|
| A61K 38/00 | (2006.01) | |
| A61K 9/00 | (2006.01) | |
| A61P 37/06 | (2006.01) | |
| C07K 14/705 | (2006.01) | |
| C07K 14/76 | (2006.01) | |

(52) U.S. Cl.
CPC ...... *C07K 14/70521* (2013.01); *A61K 9/0029* (2013.01); *A61K 9/0053* (2013.01); *A61P 37/06* (2018.01); *C07K 14/76* (2013.01); *A61K 38/00* (2013.01); *C07K 2319/30* (2013.01); *C07K 2319/31* (2013.01); *C07K 2319/50* (2013.01)

(58) Field of Classification Search
CPC .............. C07K 14/70521; C07K 14/76; C07K 2319/30; C07K 2319/50
See application file for complete search history.

(56) References Cited

U.S. PATENT DOCUMENTS 5,844,095 A 12/1998 Linsley et al.

OTHER PUBLICATIONS

Peter S. Linsley, et al., "CTLA-4 is a second receptor for the B cell activation antigen B7", Journal of Experimental Medicine, 174(3), pp. 561-569, 1991.
Search Report appended to an Office Action, which was issued to Taiwanese counterpart Application No. 110104031 by the TIPO dated Mar. 8, 2022 with an English translation thereof. Exhibit 1.
Shey-Cherng Tzou, "Development of pro-CTLA-4Ig having inflammatory tissue selectivity to treat the inflammatory diseases more safely and effectively," Internet Literature, Oct. 23, 2019, research project results report sponsored by Ministry of Science and Technology. Exhibit 2.
Marcin Poreba, "Protease-activated prodrugs: strategies, challenges, and future directions," The FEBS Journal, (Jan. 23, 2020), p. 1936-1969, vol. 287, FEBS Press. Exhibit 3.
Chen et al., "Fusion Protein Linkers: Property, Design and Functionality," Adv Drug Deliv Rev., (Oct. 15, 2013), p. 1357-1369, vol. 65 (10), NIH Public Access. Exhibit 4.

*Primary Examiner* — Dong Jiang
(74) *Attorney, Agent, or Firm* — Law Offices of Albert Wai-Kit Chan, PLLC

(57) ABSTRACT

Disclosed herein is an activatable fusion protein that includes, in an N- to C-terminal direction, an albumin, a matrix metalloproteinase-cleavable linker, and an immunoadhesin which includes a cytotoxic T lymphocyte-associated antigen-4 (CTLA4) having an N-terminal extracellular domain and an IgG Fc region, wherein the albumin is released from the activatable fusion protein in the presence of a matrix metalloproteinase that cleaves the cleavable linker, so that the N-terminal extracellular domain of the CTLA4 binds to CD80 or CD86. Also disclosed herein is use of the activatable fusion protein for suppressing a T cell-dependent immune response.

4 Claims, 4 Drawing Sheets

Specification includes a Sequence Listing.

SEQUENCE LISTING

<160> NUMBER OF SEQ ID NOS: 19

<210> SEQ ID NO 1
<211> LENGTH: 1755
<212> TYPE: DNA
<213> ORGANISM: Homo sapiens

<400> SEQUENCE: 1

| | | | | | |
|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaaacatgtg | ttgctgatga | gtcagctgaa | 180 |
| aattgtgaca | aatcacttca | tacccttttt | ggagacaaat | tatgcacagt | tgcaactctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | aacctccccc | gattggtgag | accagaggtt | 360 |
| gatgtgatgt | gcactgcttt | tcatgacaat | gaagagacat | ttttgaaaaa | atacttatat | 420 |
| gaaattgcca | agacatcc | ttacttttat | gccccggaac | tccttttctt | tgctaaaagg | 480 |
| tataaagctg | cttttacaga | atgttgccaa | gctgctgata | agctgcctg | cctgttgcca | 540 |
| aagctcgatg | aacttcggga | tgaagggaag | gcttcgtctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | cttgaatgtg | ctgatgacag | gcggacctt | 780 |
| gccaagtata | tctgtgaaaa | tcaagattcg | atctccagta | aactgaagga | atgctgtgaa | 840 |
| aaacctctgt | tggaaaaatc | ccactgcatt | gccgaagtgg | aaaatgatga | gatgcctgct | 900 |
| gacttgcctt | cattagctgc | tgattttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agagaagtgc | 1080 |
| tgtgccgctg | cagatcctca | tgaatgctat | gccaaagtgt | tcgatgaatt | taaaccctct | 1140 |
| gtggaagagc | tcagaattt | aatcaaacaa | aattgtgagc | ttttttgagca | gcttggagag | 1200 |
| tacaaattcc | agaatgcgct | attagttcgt | tacaccaaga | aagtaccccca | agtgtcaact | 1260 |
| ccaactcttg | tagaggtctc | aagaaaccta | ggaaaagtgg | gcagcaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | ctttccagct | ctggaagtcg | atgaaacata | cgttcccaaa | 1500 |
| gagtttaatg | ctgaaacgtt | caccttccat | gcagatatat | gcacactttc | tgagaaggag | 1560 |
| agacaaatca | agaaacaaac | tgcacttgtt | gagcttgtga | acacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | ctttgccgag | gagggtaaaa | aacttgttgc | tgcaagtcaa | 1740 |
| gctgccttag | gctta | | | | | 1755 |

<210> SEQ ID NO 2
<211> LENGTH: 585
<212> TYPE: PRT
<213> ORGANISM: Homo sapiens

<400> SEQUENCE: 2

Asp Ala His Lys Ser Glu Val Ala His Arg Phe Lys Asp Leu Gly Glu

```
1               5                   10                  15
Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
                35                  40                  45

Phe Ala Lys Thr Cys Val Ala Asp Glu Ser Ala Glu Asn Cys Asp Lys
                50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
                210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
                290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
                370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430
```

```
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585
```

```
<210> SEQ ID NO 3
<211> LENGTH: 533
<212> TYPE: DNA
<213> ORGANISM: Artificial Sequence
<220> FEATURE:
<223> OTHER INFORMATION: linker-CTLA4E-IgG1H DNA fragment

<400> SEQUENCE: 3
tgcccaccgt gcccagcacc cgaactcctg gggggaccgg caatgcacgt ggcacagcct      60
gcagtggtgc tggcaagctc caggggaatc gcatctttcg tgtgcgagta cgcaagccca     120
ggcaaggcaa ccgaggtgcg ggtgacagtg ctgagacagg cagactccca ggtgaccgag     180
gtgtgcgcag caacatatat gatgggcaac gagctgacct ttctggacga ttctatctgt     240
accggcacat ctagcggcaa ccaagtgaat ctgaccatcc agggcctgcg ggccatggat     300
acaggcctgt acatctgcaa ggtggagctg atgtatcccc ctccatacta tctgggcatc     360
ggcaatggca cacagatcta cgtgatcgac ccagagccct gtcctgacag cgatcaggag     420
ccaaagtcct ctgataagac ccacacaagc ccccttccc ccgcacccga actcctgggg      480
ggaccgtcag tcttcctctt ccccccaaaa cccaaggaca ccctcatgat ctc            533

<210> SEQ ID NO 4
<211> LENGTH: 580
<212> TYPE: DNA
<213> ORGANISM: Artificial Sequence
<220> FEATURE:
<223> OTHER INFORMATION: IgG1CH2-CH3 DNA fragment

<400> SEQUENCE: 4
ccggacccct gaggtcacat gcgtggtggt ggacgtgagc cacgaagacc ctgaggtcaa      60
gttcaactgg tacgtggacg gcgtggaggt gcataatgcc aagacaaagc cgcgggagga     120
gcagtacaac agcacgtacc gtgtggtcag cgtcctcacc gtcctgcacc aggactggct     180
gaatggcaag gagtacaagt gcaaggtctc caacaaagcc ctcccagccc ccatcgagaa     240
aaccatctcc aaagccaagg ggcagcccg agaaccacag gtgtacaccc tgcccccatc      300
```

| | |
|---|---|
| ccgggatgag ctgaccaaga accaggtcag cctgacctgc ctggtcaaag gcttctatcc | 360 |
| cagcgacatc gccgtggagt gggagagcaa tgggcagccg gagaacaact acaagaccac | 420 |
| gcctcccgtg ctggactccg acggctcctt cttcctctac agcaagctca ccgtggacaa | 480 |
| gagcaggtgg cagcagggga acgtcttctc atgctccgtg atgcatgagg ctctgcacaa | 540 |
| ccactacacg cagaagagcc tctccctgtc tccgggtaaa | 580 |

```
<210> SEQ ID NO 5
<211> LENGTH: 8889
<212> TYPE: DNA
<213> ORGANISM: Artificial Sequence
<220> FEATURE:
<223> OTHER INFORMATION: Plasmid pLNCX-10D1.3
<220> FEATURE:
<221> NAME/KEY: restriction_site
<222> LOCATION: (93)..(105)
<223> OTHER INFORMATION: recognized by SfiI
<220> FEATURE:
<221> NAME/KEY: coding sequence of antibody 10D1.3
<222> LOCATION: (106)..(2265)
<220> FEATURE:
<221> NAME/KEY: restriction_site
<222> LOCATION: (2266)..(2271)
<223> OTHER INFORMATION: recognized by ClaI

<400> SEQUENCE: 5
```

| | |
|---|---|
| atggagacag acacactcct gctatgggta ctgctgctct ggttccagg ttccactggt | 60 |
| gactatccat atgatgttcc agattatgct ggggcccagc cggccgaaat tgtgttgacg | 120 |
| cagtctccag gcaccctgtc tttgtctcca ggggaaagag ccaccctctc ctgcagggcc | 180 |
| agtcagagtg ttggcagcag ctacttagcc tggtaccagc agaaacctgg ccaggctccc | 240 |
| aggctcctca tctatggtgc attcagcagg gccactggca tcccagacag gttcagtggc | 300 |
| agtgggtctg ggacagactt cactctcacc atcagcagac tggagcctga agattttgca | 360 |
| gtgtattact gtcagcagta tggtagctca ccgtggacgt tcggccaagg gaccaaggtg | 420 |
| gaaatcaaac ggactgtggc tgcaccatct gtcttcatct tcccgccatc tgatgagcag | 480 |
| ttgaaatctg gaactgcctc tgttgtgtgc ctgctgaata acttctatcc cagagaggcc | 540 |
| aaagtacagt ggaaggtgga taacgccctc caatcgggta actcccagga gagtgtcaca | 600 |
| gagcaggaca gcaaggacag cacctacagc ctcagcagca ccctgacgct gagcaaagca | 660 |
| gactacgaga aacacaaact ctacgcctgc gaagtcaccc atcagggcct gagctcgccc | 720 |
| gtcacaaaga gcttcaacag gggagagtgc ctcgagcgag caaaacgagc accagtaaaa | 780 |
| caaacactaa acttcgacct actaaaacta gcaggagacg tagaatcaaa cccaggacca | 840 |
| gccacaacca tggagacaga cacactcctg ctatgggtac tgctgctctg gttccaggt | 900 |
| tccactggtg acagatctca ggtgcagctg gtggagtctg gggaggcgt ggtccagcct | 960 |
| ggaggtcccc tgagactctc ctgtgcagcc tctggattca ccttcagtag ctatactatg | 1020 |
| cactgggtcc gccaggctcc aggcaagggg ctggagtggg tgacatttat atcatatgat | 1080 |
| ggaaacaata atactacgc agactccgtg aagggccgat tcaccatctc cagagacaat | 1140 |
| tccaagaaca cgctgtatct gcaaatgaac agcctgagag ctgaggacac ggctatatat | 1200 |
| tactgtgcga ggaccggctg ctggggccc tttgactact ggggccaggg aaccctggtc | 1260 |
| accgtctcct cagcctccac caagggacca tcggtcttcc ccctggcacc ctcctccaag | 1320 |
| agcacctctg ggggcacagc ggccctgggc tgcctggtca aggactactt ccccgaaccg | 1380 |
| gtgacggtgt cgtggaactc aggcgccctg accagcggcg tgcacacctt cccggctgtc | 1440 |

```
ctacagtcct caggactcta ctccctcagc agcgtggtga ccgtgccctc cagcagcttg    1500
ggcacccaga cctacatctg caacgtgaat cacaagccca gcaacaccaa ggtcgacaag    1560
aaagttgagc ccaaatcttg tgacaaaact cacacatgcc caccgtgccc agcacccgaa    1620
ctcctggggg gaccgtcagt cttcctcttc cccccaaaac ccaaggacac cctcatgatc    1680
tcccggaccc ctgaggtcac atgcgtggtg gtggacgtga gccacgaaga ccctgaggtc    1740
aagttcaact ggtacgtgga cggcgtggag gtgcataatg ccaagacaaa gccgcgggag    1800
gagcagtaca acagcacgta ccgtgtggtc agcgtcctca ccgtcctgca ccaggactgg    1860
ctgaatggca aggagtacaa gtgcaaggtc tccaacaaag ccctcccagc ccccatcgag    1920
aaaaccatct ccaaagccaa ggggcagccc cgagaaccac aggtgtacac cctgccccca    1980
tcccgggatg agctgaccaa gaaccaggtc agcctgacct gcctggtcaa aggcttctat    2040
cccagcgaca tcgccgtgga gtgggagagc aatgggcagc cggagaacaa ctacaagacc    2100
acgcctcccg tgctggactc cgacggctcc ttcttcctct acagcaagct caccgtggac    2160
aagagcaggt ggcagcaggg gaacgtcttc tcatgctccg tgatgcatga ggctctgcac    2220
aaccactaca cgcagaagag cctctccctg tctccgggta aataaatcga taaaataaaa    2280 gatttattt agtctccaga aaaggggggg aatgaaagac cccacctgta ggtttggcaa    2340
gctagcttaa gtaacgccat tttgcaaggc atggaaaaat acataactga aatagagaa    2400 gttcagatca aggtcaggaa cagatggaac agctgaatat gggccaaaca ggatatctgt    2460
ggtaagcagt tcctgccccg gctcagggcc aagaacagat ggaacagctg aatatgggcc    2520
aaacaggata tctgtggtaa gcagttcctg ccccggctca gggccaagaa cagatggtcc    2580
ccagatgcgg tccagccctc agcagtttct agagaaccat cagatgtttc cagggtgccc    2640
caaggacctg aaatgaccct gtgccttatt tgaactaacc aatcagttcg cttctcgctt    2700
ctgttcgcgc gcttctgctc cccgagctca ataaaagagc ccacaacccc tcactcgggg    2760
cgccagtcct ccgattgact gagtcgcccg ggtacccgtg tatccaataa accctcttgc    2820
agttgcatcc gacttgtggt ctcgctgttc cttgggaggg tctcctctga gtgattgact    2880
acccgtcagc gggggtcttt catttggggg ctcgtccggg atcggggagac ccctgcccag    2940 ggaccaccga cccaccaccg ggaggtaagc tggctgcctc gcgcgtttcg gtgatgacgg    3000
tgaaaacctc tgacacatgc agctcccgga cggtcacag cttgtctgt aagcggatgc    3060 cgggagcaga caagcccgtc agggcgcgtc agcgggtgtt ggcgggtgtc ggggcgcagc    3120
catgacccag tcacgtagcg atagcggagt gtatactggc ttaactatgc ggcatcagag    3180
cagattgtac tgagagtgca ccatatgcgg tgtgaaatac cgcacagatg cgtaaggaga    3240
aaataccgca tcaggcgctc ttccgcttcc tcgctcactg actcgctgcg ctcggtcgtt    3300
cggctgcggc gagcggtatc agctcactca aaggcggtaa tacggttatc cacagaatca    3360
ggggataacg caggaaagaa catgtgagca aaaggccagc aaaaggccag gaaccgtaaa    3420
aaggccgcgt tgctggcgtt tttccatagg ctccgccccc ctgacgagca tcacaaaaat    3480
cgacgctcaa gtcagaggtg gcgaaacccg acaggactat aaagatacca ggcgtttccc    3540
cctggaagct ccctcgtgcg ctctcctgtt ccgaccctgc cgcttaccgg atacctgtcc    3600
gcctttctcc cttcgggaag cgtggcgctt tctcatagct cacgctgtag gtatctcagt    3660
tcggtgtagg tcgttcgctc caagctgggc tgtgtgcacg aaccccccgt tcagcccgac    3720
cgctgcgcct tatccggtaa ctatcgtctt gagtccaacc cggtaagaca cgacttatcg    3780
ccactggcag cagccactgg taacaggatt agcagagcga ggtatgtagg cggtgctaca    3840
```

```
gagttcttga agtggtggcc taactacggc tacactagaa ggacagtatt tggtatctgc    3900
gctctgctga agccagttac cttcggaaaa agagttggta gctcttgatc cggcaaacaa    3960
accaccgctg gtagcggtgg ttttttttgtt tgcaagcagc agattacgcg cagaaaaaaa    4020
ggatctcaag aagatccttt gatcttttct acggggtctg acgctcagtg gaacgaaaac    4080
tcacgttaag ggattttggt catgagatta tcaaaaagga tcttcaccta gatcctttta    4140
aattaaaaat gaagttttaa atcaatctaa agtatatatg agtaaacttg gtctgacagt    4200
taccaatgct taatcagtga ggcacctatc tcagcgatct gtctatttcg ttcatccata    4260
gttgcctgac tccccgtcgt gtagataact acgatacggg agggcttacc atctggcccc    4320
agtgctgcaa tgataccgcg agacccacgc tcaccggctc cagatttatc agcaataaac    4380
cagccagccg gaagggccga gcgcagaagt ggtcctgcaa ctttatccgc ctccatccag    4440
tctattaatt gttgccggga agctagagta agtagttcgc cagttaatag tttgcgcaac    4500
gttgttgcca ttgctgcagg catcgtggtg tcacgctcgt cgtttggtat ggcttcattc    4560
agctccggtt cccaacgatc aaggcgagtt acatgatccc ccatgttgtg caaaaaagcg    4620
gttagctcct tcggtcctcc gatcgttgtc agaagtaagt tggccgcagt gttatcactc    4680
atggttatgg cagcactgca taattctctt actgtcatgc catccgtaag atgcttttct    4740
gtgactggtg agtactcaac caagtcattc tgagaatagt gtatgcggcg accgagttgc    4800
tcttgcccgg cgtcaacacg ggataatacc gcgccacata gcagaacttt aaaagtgctc    4860
atcattggaa aacgttcttc ggggcgaaaa ctctcaagga tcttaccgct gttgagatcc    4920
agttcgatgt aacccactcg tgcacccaac tgatcttcag catcttttac tttcaccagc    4980
gtttctgggt gagcaaaaac aggaaggcaa aatgccgcaa aaaagggaat aagggcgaca    5040
cggaaatgtt gaatactcat actcttcctt tttcaatatt attgaagcat ttatcagggt    5100
tattgtctca tgagcggata catatttgaa tgtatttaga aaaataaaca aataggggtt    5160
ccgcgcacat ttccccgaaa agtgccacct gacgtctaag aaaccattat tatcatgaca    5220
ttaacctata aaaataggcg tatcacgagg ccctttcgtc ttcaagaatt cataccagat    5280
caccgaaaac tgtcctccaa atgtgtcccc ctcacactcc caaattcgcg gcttctgcc    5340 tcttagacca ctctacccta ttccccacac tcaccggagc caaagccgcg gcccttccgt    5400
ttctttgctt ttgaaagacc ccaccccgtag gtggcaagct agcttaagta acgccacttt    5460
gcaaggcatg gaaaaataca taactgagaa tagaaaagtt cagatcaagg tcaggaacaa    5520
agaaacagct gaataccaaa caggatatct gtggtaagcg gttcctgccc cggctcaggg    5580
ccaagaacag atgagacagc tgagtgatgg gccaaacagg atatctgtgg taagcagttc    5640
ctgccccggc tcggggccaa gaacagatgg tccccagatg cggtccagcc ctcagcagtt    5700
tctagtgaat catcagatgt ttccagggtg ccccaaggac ctgaaaatga ccctgtacct    5760
tatttgaact aaccaatcag ttcgcttctc gcttctgttc gcgcgcttcc gctctccgag    5820
ctcaataaaa gagcccacaa cccctcactc ggcgcgccag tcttccgata gactgcgtcg    5880
cccgggtacc cgtattccca ataaagcctc ttgctgtttg catccgaatc gtggtctcgc    5940
tgttccttgg gagggtctcc tctgagtgat tgactaccca cgacggggt ctttcatttg    6000 ggggctcgtc cgggatttgg agaccctgc ccagggacca ccgacccacc accgggaggt    6060
aagctggcca gcaacttatc tgtgtctgtc cgattgtcta gtgtctatgt ttgatgttat    6120
gcgcctgcgt ctgtactagt tagctaacta gctctgtatc tggcggaccc gtggtggaac    6180
```

```
tgacgagttc tgaacacccg gccgcaaccc tgggagacgt cccagggact tgggggccg      6240 ttttttgtggc ccgacctgag gaagggagtc gatgtggaat ccgacccccgt caggatatgt    6300 ggttctggta ggagacgaga acctaaaaca gttcccgcct ccgtctgaat ttttgctttc     6360
ggtttggaac cgaagccgcg cgtcttgtct gctgcagcgc tgcagcatcg ttctgtgttg    6420
tctctgtctg actgtgtttc tgtatttgtc tgaaaattag ggccagactg ttaccactcc    6480
cttaagtttg accttaggtc actggaaaga tgtcgagcgg atcgctcaca accagtcggt    6540
agatgtcaag aagagacgtt gggttacctt ctgctctgca gaatggccaa cctttaacgt    6600
cggatggccg cgagacggca cctttaaccg agacctcatc acccaggtta agatcaaggt    6660
cttttcacct ggcccgcatg gacacccaga ccaggtcccc tacatcgtga cctgggaagc    6720
cttggctttt gaccccccctc cctgggtcaa gcccttttgta caccctaagc ctccgcctcc    6780
tcttcctcca tccgcccgt ctctccccct tgaacctcct cgttcgaccc cgcctcgatc     6840
ctccctttat ccagccctca ctccttctct aggcgccgga attccgatct gatcaagaga    6900
caggatgagg atcgtttcgc atgattgaac aagatggatt gcacgcaggt tctccggccg    6960
cttgggtgga gaggctattc ggctatgact gggcacaaca gacaatcggc tgctctgatg    7020
ccgccgtgtt ccggctgtca gcgcaggggc gcccggttct ttttgtcaag accgacctgt    7080
ccggtgccct gaatgaactg caggacgagg cagcgcggct atcgtggctg gccacgacgg    7140
gcgttccttg cgcagctgtg ctcgacgttg tcactgaagc gggaagggac tggctgctat    7200
tgggcgaagt gccggggcag gatctcctgt catctcacct tgctcctgcc gagaaagtat    7260
ccatcatggc tgatgcaatg cggcggctgc atacgcttga tccggctacc tgcccattcg    7320
accaccaagc gaaacatcgc atcgagcgag cacgtactcg gatggaagcc ggtcttgtcg    7380
atcaggatga tctggacgaa gagcatcagg ggctcgcgcc agccgaactg ttcgccaggc    7440
tcaaggcgcg catgcccgac ggcgaggatc tcgtcgtgac ccatggcgat gcctgcttgc    7500
cgaatatcat ggtggaaaat ggccgctttt ctggattcat cgactgtggc cggctgggtg    7560
tggcggaccg ctatcaggac atagcgttgg ctacccgtga tattgctgaa gagcttggcg    7620
gcgaatgggc tgaccgcttc ctcgtgcttt acggtatcgc cgctcccgat tcgcagcgca    7680
tcgccttcta tcgccttctt gacgagttct tctgagcggg actctggggt tcgaaatgac    7740
cgaccaagcg acgcccaacc tgccatcacg agatttcgat tccaccgccg ccttctatga    7800
aaggttgggc ttcggaatcg ttttccggga cgccggctgg atgatcctcc agcgcgggga    7860
tctcatgctg gagttcttcg cccacccccgg gctcgatccc ctcgcgagtt ggttcagctg    7920
ctgcctgagg ctggacgacc tcgcggagtt ctaccggcag tgcaaatccg tcggcatcca    7980
ggaaaccagc agcggctatc cgcgcatcca tgcccccgaa ctgcaggagt ggggaggcac    8040
gatggccgct ttggtcgagg cggatccggc cattagccat attattcatt ggttatatag    8100
cataaatcaa tattggctat tggccattgc atacgttgta tccatatcat aatatgtaca    8160
tttatattgg ctcatgtcca acattaccgc catgttgaca ttgattattg actagttatt    8220
aatagtaatc aattacgggg tcattagttc atagcccata tatggagttc cgcgttacat    8280
aacttacggt aaatggcccg cctggctgac cgcccaacga ccccccgccca ttgacgtcaa    8340 taatgacgta tgttcccata gtaacgccaa tagggacttt ccattgacgt caatgggtgg    8400
agtatttacg gtaaactgcc cacttggcag tacatcaagt gtatcatatg ccaagtacgc    8460
cccctattga cgtcaatgac ggtaaatggc ccgcctggca ttatgcccag tacatgacct    8520
tatgggactt tcctacttgg cagtacatct acgtattagt catcgctatt accatggtga    8580
```

```
tgcggttttg gcagtacatc aatgggcgtg gatagcggtt tgactcacgg ggatttccaa    8640
gtctccaccc cattgacgtc aatgggagtt tgttttggca ccaaaatcaa cgggactttc    8700
caaaatgtcg taacaactcc gccccattga cgcaaatggg cggtaggcat gtacggtggg    8760
aggtctatat aagcagagct cgtttagtga accgtcagat cgcctggaga cgccatccac    8820
gctgttttga cctccataga agacaccggg accgatccag cctccgcggc cccaagcttg    8880
ttatccacc                                                            8889
```

<210> SEQ ID NO 6
<211> LENGTH: 21
<212> TYPE: PRT
<213> ORGANISM: Artificial Sequence
<220> FEATURE:
<223> OTHER INFORMATION: Igk secretion signal peptide

<400> SEQUENCE: 6

Met Glu Thr Asp Thr Leu Leu Leu Trp Val Leu Leu Leu Trp Val Pro
 1               5                  10                  15

Gly Ser Thr Gly Asp
            20

<210> SEQ ID NO 7
<211> LENGTH: 39
<212> TYPE: DNA
<213> ORGANISM: Artificial Sequence
<220> FEATURE:
<223> OTHER INFORMATION: Forward primer F1 for PCR amplification of ALB
      gene
<220> FEATURE:
<221> NAME/KEY: restriction_site
<222> LOCATION: (5)..(17)
<223> OTHER INFORMATION: recognized by SfiI

<400> SEQUENCE: 7
cgtaggccca gccggccgat gcacacaaga gtgaggttg                            39

<210> SEQ ID NO 8
<211> LENGTH: 31
<212> TYPE: DNA
<213> ORGANISM: Artificial Sequence
<220> FEATURE:
<223> OTHER INFORMATION: Reverse primer R1 for PCR amplification of ALB
      gene

<400> SEQUENCE: 8
cacggtgggc ataagcctaa ggcagcttga c                                   31

<210> SEQ ID NO 9
<211> LENGTH: 21
<212> TYPE: DNA
<213> ORGANISM: Artificial Sequence
<220> FEATURE:
<223> OTHER INFORMATION: Forward primer F2 for PCR amplification of
      linker-CTLA4E-IgG1H DNA fragment

<400> SEQUENCE: 9
cttaggctta tgcccaccgt g                                              21

<210> SEQ ID NO 10
<211> LENGTH: 21
<212> TYPE: DNA
<213> ORGANISM: Artificial Sequence
<220> FEATURE:
<223> OTHER INFORMATION: Reverse primer R2 for PCR amplification of linker-CTLA4E-IgG1H DNA fragment

<400> SEQUENCE: 10
gagatcatga gggtgtcctt g                                                21

<210> SEQ ID NO 11
<211> LENGTH: 21
<212> TYPE: DNA
<213> ORGANISM: Artificial Sequence
<220> FEATURE:
<223> OTHER INFORMATION: Forward primer F3 for PCR amplification of
      IgG1CH2-CH3 DNA fragment

<400> SEQUENCE: 11
caaggacacc ctcatgatct c                                                21

<210> SEQ ID NO 12
<211> LENGTH: 53
<212> TYPE: DNA
<213> ORGANISM: Artificial Sequence
<220> FEATURE:
<223> OTHER INFORMATION: Reverse primer R3 for PCR amplification of
      IgG1CH2-CH3 DNA fragment
<220> FEATURE:
<221> NAME/KEY: restriction_site
<222> LOCATION: (6)..(11)
<223> OTHER INFORMATION: recognized by ClaI

<400> SEQUENCE: 12
gtcatatcga ttcaatggtg atggtgatga tgtttacccg agacaggga gag              53

<210> SEQ ID NO 13
<211> LENGTH: 2305
<212> TYPE: DNA
<213> ORGANISM: Artificial Sequence
<220> FEATURE:
<223> OTHER INFORMATION: PCR product A4

<400> SEQUENCE: 13
cgtaggccca gccggccgat gcacacaaga gtgaggttgc tcatcggttt aaagatttgg      60
gagaagaaaa tttcaaagcc ttggtgttga ttgcctttgc tcagtatctt agcagtgtc     120 cattttgaaga tcatgtaaaa ttagtgaatg aagtaactga atttgcaaaa acatgtgttg    180
ctgatgagtc agctgaaaat tgtgacaaat cacttcatac cctttttgga gacaaattat    240
gcacagttgc aactcttcgt gaaacctatg gtgaaatggc tgactgctgt gcaaaacaag    300
aacctgagag aaatgaatgc ttcttgcaac acaaagatga caccaaac ctcccccgat     360 tggtgagacc agaggttgat gtgatgtgca ctgcttttca tgacaatgaa gagacatttt    420
tgaaaaaata cttatatgaa attgccagaa gacatcctta cttttatgcc ccggaactcc    480
ttttctttgc taaaaggtat aaagctgctt ttacagaatg ttgccaagct gctgataaag    540
ctgcctgcct gttgccaaag ctcgatgaac ttcgggatga agggaaggct tcgtctgcca    600
aacagagact caagtgtgcc agtctccaaa aatttggaga aagagctttc aaagcatggg    660
cagtagctcg cctgagccag agatttccca agctgagtt tgcagaagtt tccaagttag    720
tgacagatct taccaaagtc cacacggaat gctgccatgg agatctgctt gaatgtgctg    780
atgacagggc ggaccttgcc aagtatatct gtgaaaatca agattcgatc tccagtaaac    840
tgaaggaatg ctgtgaaaaa cctctgttgg aaaaatccca ctgcattgcc gaagtggaaa    900
atgatgagat gcctgctgac ttgccttcat tagctgctga ttttgttgaa agtaaggat     960 tttgcaaaaa ctatgctgag gcaaaggatg tcttcctggg catgtttttg tatgaatatg   1020

-continued

```
caagaaggca tcctgattac tctgtcgtgc tgctgctgag acttgccaag acatatgaaa    1080
ccactctaga gaagtgctgt gccgctgcag atcctcatga atgctatgcc aaagtgttcg    1140
atgaatttaa acctcttgtg gaagagcctc agaatttaat caaacaaaat tgtgagcttt    1200
ttgagcagct tggagagtac aaattccaga atgcgctatt agttcgttac accaagaaag    1260 tacccccaagt gtcaactcca actcttgtag aggtctcaag aaacctagga aaagtgggca    1320
gcaaatgttg taaacatcct gaagcaaaaa gaatgccctg tcagaagac tatctatccg     1380 tggtcctgaa ccagttatgt gtgttgcatg agaaaacgcc agtaagtgac agagtcacca    1440
aatgctgcac agaatccttg gtgaacaggc gaccatgctt tcagctctg gaagtcgatg     1500 aaacatacgt tcccaaagag tttaatgctg aaacgttcac cttccatgca gatatatgca    1560
cactttctga gaaggagaga caaatcaaga acaaaactgc acttgttgag cttgtgaaac    1620
acaagcccaa ggcaacaaaa gagcaactga aagctgttat ggatgatttc gcagcttttg    1680
tagagaagtg ctgcaaggct gacgataagg agacctgctt tgccgaggag ggtaaaaaac    1740
ttgttgctgc aagtcaagct gccttaggct tatgcccacc gtgcccagca cccgaactcc    1800 tgggggacc ggcaatgcac gtggcacagc ctgcagtggt gctggcaagc tccaggggaa     1860
tcgcatcttt cgtgtgcgag tacgcaagcc caggcaaggc aaccgaggtg cgggtgacag    1920
tgctgagaca ggcagactcc caggtgaccg aggtgtgcgc agcaacatat atgatgggca    1980
acgagctgac ctttctggac gattctatct gtaccggcac atctagcggc aaccaagtga    2040
atctgaccat ccagggcctg cgggccatgg atacaggcct gtacatctgc aaggtggagc    2100
tgatgtatcc ccctccatac tatctgggca tcggcaatgg cacacagatc tacgtgatcg    2160
acccagagcc ctgtcctgac agcgatcagg agccaaagtc ctctgataag acccacacaa    2220 gcccccttc ccccgcaccc gaactcctgg ggggaccgtc agtcttcctc ttcccccaa      2280 aacccaagga caccctcatg atctc                                         2305
```

<210> SEQ ID NO 14
<211> LENGTH: 2917
<212> TYPE: DNA
<213> ORGANISM: Artificial Sequence
<220> FEATURE:
<223> OTHER INFORMATION: PCR product A5

<400> SEQUENCE: 14

```
cgtaggccca gccggccgat gcacacaaga gtgaggttgc tcatcggttt aaagatttgg      60
gagaagaaaa tttcaaagcc ttggtgttga ttgcctttgc tcagtatctt cagcagtgtc     120
catttgaaga tcatgtaaaa ttagtgaatg aagtaactga atttgcaaaa acatgtgttg    180
ctgatgagtc agctgaaaat tgtgacaaat cacttcatac ccttttttgga gacaaattat    240 gcacagttgc aactcttcgt gaaacctatg gtgaaatggc tgactgctgt gcaaaacaag    300
aacctgagag aaatgaatgc ttcttgcaac acaaagatga caacccaaac ctcccccgat    360
tggtgagacc agaggttgat gtgatgtgca ctgcttttca tgacaatgaa gagacatttt    420
tgaaaaaata cttatatgaa attgccagaa gacatcctta cttttatgcc ccggaactcc    480
ttttctttgc taaaggtat aaagctgctt ttacagaatg ttgccaagct gctgataaag      540
ctgcctgcct gttgccaaag ctcgatgaac ttcgggatga agggaaggct tcgtctgcca     600
aacagagact caagtgtgcc agtctcccaaa aatttggaga agagctttc aaagcatggg     660 cagtagctcg cctgagccag agatttccca agctgagtt tgcagaagtt tccaagttag      720
```

```
tgacagatct taccaaagtc cacacggaat gctgccatgg agatctgctt gaatgtgctg      780
atgacagggc ggaccttgcc aagtatatct gtgaaaatca agattcgatc tccagtaaac      840
tgaaggaatg ctgtgaaaaa cctctgttgg aaaaatccca ctgcattgcc gaagtggaaa      900
atgatgagat gcctgctgac ttgccttcat tagctgctga ttttgttgaa agtaaggatg      960
tttgcaaaaa ctatgctgag gcaaaggatg tcttcctggg catgttttg tatgaatatg     1020 caagaaggca tcctgattac tctgtcgtgc tgctgctgag acttgccaag acatatgaaa     1080
ccactctaga gaagtgctgt gccgctgcag atcctcatga atgctatgcc aaagtgttcg     1140
atgaatttaa acctcttgtg gaagagcctc agaatttaat caaacaaaat tgtgagcttt     1200
ttgagcagct tggagagtac aaattccaga atgcgctatt agttcgttac accaagaaag     1260 tacccccaagt gtcaactcca actcttgtag aggtctcaag aaacctagga aaagtgggca     1320
gcaaatgttg taaacatcct gaagcaaaaa gaatgccctg tgcagaagac tatctatccg     1380
tggtcctgaa ccagttatgt gtgttgcatg agaaaacgcc agtaagtgac agagtcacca     1440
aatgctgcac agaatccttg gtgaacaggc gaccatgctt tcagctctg gaagtcgatg     1500 aaacatacgt tcccaaagag tttaatgctg aaacgttcac cttccatgca gatatatgca     1560
cactttctga gaaggagaga caaatcaaga acaaactgc acttgttgag cttgtgaaac     1620
acaagcccaa ggcaacaaaa gagcaactga agctgttat ggatgatttc gcagcttttg     1680
tagagaagtg ctgcaaggct gacgataagg agacctgctt tgccgaggag ggtaaaaaac     1740
ttgttgctgc aagtcaagct gccttaggct tatgcccacc gtgcccagca cccgaactcc     1800 tgggggggacc ggcaatgcac gtggcacagc ctgcagtggt gctggcaagc tccagggggaa   1860 tcgcatcttt cgtgtgcgag tacgcaagcc caggcaaggc aaccgaggtg cgggtgacag     1920
tgctgagaca ggcagactcc caggtgaccg aggtgtgcgc agcaacatat atgatgggca     1980
acgagctgac ctttctggac gattctatct gtaccggcac atctagcggc aaccaagtga     2040
atctgaccat ccagggcctg cgggccatgg atacaggcct gtacatctgc aaggtggagc     2100
tgatgtatcc ccctccatac tatctgggca tcggcaatgg cacacagatc tacgtgatcg     2160
acccagagcc ctgtcctgac agcgatcagg agccaaagtc ctctgataag acccacacaa     2220 gcccccttc ccccgcaccc gaactcctgg ggggaccgtc agtcttcctc ttcccccca     2280 aacccaagga cacccctatg atctcccgga ccccctgaggt cacatgcgtg gtggtggacg     2340
tgagccacga agaccctgag gtcaagttca actggtacgt ggacggcgtg gaggtgcata     2400
atgccaagac aaagccgcgg gaggagcagt acaacagcac gtaccgtgtg gtcagcgtcc     2460
tcaccgtcct gcaccaggac tggctgaatg gcaaggagta caagtgcaag gtctccaaca     2520
aagccctccc agccccatc gagaaaacca tctccaaagc caaggggcag ccccgagaac     2580
cacaggtgta caccctgccc ccatcccggg atgagctgac caagaaccag gtcagcctga     2640
cctgcctggt caaaggcttc tatcccagcg acatcgccgt ggagtgggag agcaatgggc     2700
agccggagaa caactacaag accacgcctc ccgtgctgga ctccgacggc tccttcttcc     2760
tctacagcaa gctcaccgtg gacaagagca ggtggcagca ggggaacgtc ttctcatgct     2820
ccgtgatgca tgaggctctg cacaaccact acacgcagaa gagcctctcc ctgtctccgg     2880
gtaaacatca tcaccatcac cattgaatcg atatgac                              2917
```

<210> SEQ ID NO 15
<211> LENGTH: 956
<212> TYPE: PRT
<213> ORGANISM: Artificial Sequence
<220> FEATURE:
<223> OTHER INFORMATION: fusion protein ALB-linker-CTLA4-Ig

<400> SEQUENCE: 15

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Cys Pro Pro Cys Pro Ala Pro
            580                 585                 590

Glu Leu Leu Gly Gly Pro Ala Met His Val Ala Gln Pro Ala Val Val
                595                 600                 605

Leu Ala Ser Ser Arg Gly Ile Ala Ser Phe Val Cys Glu Tyr Ala Ser
            610                 615                 620

Pro Gly Lys Ala Thr Glu Val Arg Val Thr Val Leu Arg Gln Ala Asp
625                 630                 635                 640

Ser Gln Val Thr Glu Val Cys Ala Ala Thr Tyr Met Met Gly Asn Glu
                645                 650                 655

Leu Thr Phe Leu Asp Asp Ser Ile Cys Thr Gly Thr Ser Ser Gly Asn
            660                 665                 670

Gln Val Asn Leu Thr Ile Gln Gly Leu Arg Ala Met Asp Thr Gly Leu
        675                 680                 685

Tyr Ile Cys Lys Val Glu Leu Met Tyr Pro Pro Pro Tyr Tyr Leu Gly
        690                 695                 700

Ile Gly Asn Gly Thr Gln Ile Tyr Val Ile Asp Pro Glu Pro Cys Pro
705                 710                 715                 720

Asp Ser Asp Gln Glu Pro Lys Ser Ser Asp Lys Thr His Thr Ser Pro
                725                 730                 735

Pro Ser Pro Ala Pro Glu Leu Leu Gly Gly Pro Ser Val Phe Leu Phe
            740                 745                 750

Pro Pro Lys Pro Lys Asp Thr Leu Met Ile Ser Arg Thr Pro Glu Val
        755                 760                 765

Thr Cys Val Val Val Asp Val Ser His Glu Asp Pro Glu Val Lys Phe
        770                 775                 780

Asn Trp Tyr Val Asp Gly Val Glu Val His Asn Ala Lys Thr Lys Pro
785                 790                 795                 800

Arg Glu Glu Gln Tyr Asn Ser Thr Tyr Arg Val Val Ser Val Leu Thr
                805                 810                 815
```

```
Val Leu His Gln Asp Trp Leu Asn Gly Lys Glu Tyr Lys Cys Lys Val
            820                 825                 830

Ser Asn Lys Ala Leu Pro Ala Pro Ile Glu Lys Thr Ile Ser Lys Ala
            835                 840                 845

Lys Gly Gln Pro Arg Glu Pro Gln Val Tyr Thr Leu Pro Pro Ser Arg
        850                 855                 860

Asp Glu Leu Thr Lys Asn Gln Val Ser Leu Thr Cys Leu Val Lys Gly
865                 870                 875                 880

Phe Tyr Pro Ser Asp Ile Ala Val Glu Trp Glu Ser Asn Gly Gln Pro
                885                 890                 895

Glu Asn Asn Tyr Lys Thr Thr Pro Pro Val Leu Asp Ser Asp Gly Ser
            900                 905                 910

Phe Phe Leu Tyr Ser Lys Leu Thr Val Asp Lys Ser Arg Trp Gln Gln
        915                 920                 925

Gly Asn Val Phe Ser Cys Ser Val Met His Glu Ala Leu His Asn His
930                 935                 940

Tyr Thr Gln Lys Ser Leu Ser Leu Ser Pro Gly Lys
945                 950                 955
```

<210> SEQ ID NO 16
<211> LENGTH: 14
<212> TYPE: PRT
<213> ORGANISM: Artificial Sequence
<220> FEATURE:
<223> OTHER INFORMATION: MMP cleavable linker

<400> SEQUENCE: 16

```
Cys Pro Pro Cys Pro Ala Pro Glu Leu Leu Gly Gly Pro Ala
1               5                   10
```

<210> SEQ ID NO 17
<211> LENGTH: 125
<212> TYPE: PRT
<213> ORGANISM: Artificial Sequence
<220> FEATURE:
<223> OTHER INFORMATION: N-terminal extracellular domain of CTLA4

<400> SEQUENCE: 17

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln
        115                 120                 125
```

<210> SEQ ID NO 18
<211> LENGTH: 232
<212> TYPE: PRT
<213> ORGANISM: Artificial Sequence
<220> FEATURE:
<223> OTHER INFORMATION: IgG1 Fc region

<400> SEQUENCE: 18

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 19
<211> LENGTH: 9618
<212> TYPE: DNA
<213> ORGANISM: Artificial Sequence
<220> FEATURE:
<223> OTHER INFORMATION: recombinant plasmid pLNCX-ALB-linker-CTLA4-Ig
<220> FEATURE:
<221> NAME/KEY: restriction_site
<222> LOCATION: (93)..(105)
<223> OTHER INFORMATION: recognized by SfiI
<220> FEATURE:
<221> NAME/KEY: ALB gene
<222> LOCATION: (106)..(1860)
<220> FEATURE:
<221> NAME/KEY: MMP cleavage linker
<222> LOCATION: (1861)..(1899)
<220> FEATURE:
<221> NAME/KEY: CTLA4 N-terminal ECD
<222> LOCATION: (1900)..(2274)
<220> FEATURE:
<221> NAME/KEY: IgG1 Fc region
<222> LOCATION: (2275)..(2973)
<220> FEATURE:
<221> NAME/KEY: restriction_site
<222> LOCATION: (2995)..(3000)
<223> OTHER INFORMATION: recognized by ClaI
<220> FEATURE:
<221> NAME/KEY: restriction_site
<222> LOCATION: (9603)..(9608)
<223> OTHER INFORMATION: recognized by HindIII

<400> SEQUENCE: 19

| | | | | | |
|---|---|---|---|---|---|
| atggagacag | acacactcct | gctatgggta | ctgctgctct | gggttccagg | ttccactggt | 60 |
| gactatccat | atgatgttcc | agattatgct | ggggcccagc | cggccgatgc | acacaagagt | 120 |
| gaggttgctc | atcggtttaa | agatttggga | agagaaaatt | tcaaagcctt | ggtgttgatt | 180 |
| gcctttgctc | agtatcttca | gcagtgtcca | tttgaagatc | atgtaaaatt | agtgaatgaa | 240 |
| gtaactgaat | ttgcaaaaac | atgtgttgct | gatgagtcag | ctgaaaattg | tgacaaatca | 300 |
| cttcataccc | tttttggaga | caaattatgc | acagttgcaa | ctcttcgtga | aacctatggt | 360 |
| gaaatggctg | actgctgtgc | aaaacaagaa | cctgagagaa | atgaatgctt | cttgcaacac | 420 |
| aaagatgaca | acccaaacct | ccccgattg | gtgagaccag | aggttgatgt | gatgtgcact | 480 |
| gcttttcatg | acaatgaaga | cacttttttg | aaaaaatact | tatatgaaat | tgccagaaga | 540 |
| catccttact | tttatgcccc | ggaactcctt | ttctttgcta | aaaggtataa | agctgctttt | 600 |
| acagaatgtt | gccaagctgc | tgataaagct | gcctgcctgt | tgccaaagct | cgatgaactt | 660 |
| cgggatgaag | ggaaggcttc | gtctgccaaa | cagagactca | agtgtgccag | tctccaaaaa | 720 |
| tttggagaaa | gagctttcaa | agcatgggca | gtagctcgcc | tgagccagag | atttcccaaa | 780 |
| gctgagtttg | cagaagtttc | caagttagtg | acagatctta | ccaaagtcca | cacgaatgc | 840 |
| tgccatggag | atctgcttga | atgtgctgat | gacagggcgg | accttgccaa | gtatatctgt | 900 |
| gaaaatcaag | attcgatctc | cagtaaactg | aaggaatgct | gtgaaaaacc | tctgttggaa | 960 |
| aaatcccact | gcattgccga | agtggaaaat | gatgagatgc | ctgctgactt | gccttcatta | 1020 |
| gctgctgatt | ttgttgaaag | taaggatgtt | tgcaaaaact | atgctgaggc | aaaggatgtc | 1080 |
| ttcctgggca | tgtttttgta | tgaatatgca | agaaggcatc | ctgattactc | tgtcgtgctg | 1140 |
| ctgctgagac | ttgccaagac | atatgaaacc | actctagaga | agtgctgtgc | cgctgcagat | 1200 |
| cctcatgaat | gctatgccaa | agtgttcgat | gaatttaaac | ctcttgtgga | agagcctcag | 1260 |
| aatttaatca | acaaaattg | tgagcttttt | gagcagcttg | gagagtacaa | attccagaat | 1320 |
| gcgctattag | ttcgttacac | caagaaagta | ccccaagtgt | caactccaac | tcttgtagag | 1380 |
| gtctcaagaa | acctaggaaa | agtgggcagc | aaatgttgta | acatcctga | agcaaaaaga | 1440 |
| atgccctgtg | cagaagacta | tctatccgtg | gtcctgaacc | agttatgtgt | gttgcatgag | 1500 |
| aaaacgccag | taagtgacag | agtcaccaaa | tgctgcacag | aatccttggt | gaacaggcga | 1560 |
| ccatgctttt | cagctctgga | agtcgatgaa | acatacgttc | ccaaagagtt | taatgctgaa | 1620 |
| acgttcacct | tccatgcaga | tatatgcaca | ctttctgaga | aggagagaca | aatcaagaaa | 1680 |
| caaactgcac | ttgttgagct | tgtgaaacac | aagcccaagg | caacaaaaga | gcaactgaaa | 1740 |
| gctgttatgg | atgatttcgc | agcttttgta | gagaagtgct | gcaaggctga | cgataaggag | 1800 |
| acctgctttg | ccgaggaggg | taaaaaactt | gttgctgcaa | gtcaagctgc | cttaggctta | 1860 |
| tgcccaccgt | gcccagcacc | cgaactcctg | ggggaccgg | caatgcacgt | ggcacagcct | 1920 |
| gcagtggtgc | tggcaagctc | caggggaatc | gcatctttcg | tgtgcgagta | cgcaagccca | 1980 |
| ggcaaggcaa | ccgaggtgcg | ggtgacagtg | ctgagacagg | cagactccca | ggtgaccgag | 2040 |
| gtgtgcgcag | caacatatat | gatgggcaac | gagctgacct | ttctggacga | ttctatctgt | 2100 |
| accggcacat | ctagcggcaa | ccaagtgaat | ctgaccatcc | agggcctgcg | ggccatggat | 2160 |
| acaggcctgt | acatctgcaa | ggtggagctg | atgtatcccc | ctccatacta | tctgggcatc | 2220 |

```
ggcaatggca cacagatcta cgtgatcgac ccagagccct gtcctgacag cgatcaggag    2280
ccaaagtcct ctgataagac ccacacaagc ccccttccc ccgcacccga actcctgggg    2340
ggaccgtcag tcttcctctt cccccaaaa cccaaggaca ccctcatgat ctcccggacc    2400
cctgaggtca catgcgtggt ggtggacgtg agccacgaag accctgaggt caagttcaac    2460
tggtacgtgg acggcgtgga ggtgcataat gccaagacaa agccgcggga ggagcagtac    2520
aacagcacgt accgtgtggt cagcgtcctc accgtcctgc accaggactg gctgaatggc    2580
aaggagtaca agtgcaaggt ctccaacaaa gccctcccag cccccatcga gaaaaccatc    2640
tccaaagcca aggggcagcc ccgagaacca caggtgtaca ccctgccccc atcccgggat    2700
gagctgacca agaaccaggt cagcctgacc tgcctggtca aaggcttcta tcccagcgac    2760
atcgccgtgg agtgggagag caatgggcag ccggagaaca actacaagac cacgcctccc    2820
gtgctggact ccgacggctc cttcttcctc tacagcaagc tcaccgtgga caagagcagg    2880
tggcagcagg ggaacgtctt ctcatgctcc gtgatgcatg aggctctgca caaccactac    2940
acgcagaaga gcctctccct gtctccgggt aaacatcatc accatcacca ttgaatcgat    3000
aaaataaaag attttattta gtctccagaa aagggggga atgaaagacc ccacctgtag    3060
gtttggcaag ctagcttaag taacgccatt ttgcaaggca tggaaaaata cataactgag    3120 aatagaaag ttcagatcaa ggtcaggaac agatggaaca gctgaatatg gccaaacag    3180 gatatctgtg gtaagcagtt cctgccccgg ctcagggcca agaacagatg gaacagctga    3240
atatgggcca aacaggatat ctgtggtaag cagttcctgc cccggctcag ggccaagaac    3300
agatggtccc cagatgcggt ccagccctca gcagtttcta gagaaccatc agatgtttcc    3360
agggtgcccc aaggacctga atgaccctg tgccttattt gaactaacca atcagttcgc    3420
ttctcgcttc tgttcgcgcg cttctgctcc ccgagctcaa taaaagagcc cacaaccct    3480 cactcggggc gccagtcctc cgattgactg agtcgcccgg gtacccgtgt atccaataaa    3540
ccctcttgca gttgcatccg acttgtggtc tcgctgttcc ttgggagggt ctcctctgag    3600
tgattgacta cccgtcagcg ggggtctttc atttggggc tcgtccggga tcgggagacc    3660
cctgcccagg gaccaccgac ccaccaccgg gaggtaagct ggctgcctcg cgcgtttcgg    3720
tgatgacggt gaaaacctct gacacatgca gctcccggag acggtcacag cttgtctgta    3780
agcggatgcc gggagcagac aagcccgtca gggcgcgtca gcgggtgttg gcgggtgtcg    3840
gggcgcagcc atgacccagt cacgtagcga tagcggagtg tatactggct taactatgcg    3900
gcatcagagc agattgtact gagagtgcac catatgcggt gtgaaatacc gcacagatgc    3960
gtaaggagaa aataccgcat caggcgctct tccgcttcct cgctcactga ctcgctgcgc    4020
tcggtcgttc ggctgcggcg agcggtatca gctcactcaa aggcggtaat acggttatcc    4080
acagaatcag gggataacgc aggaaagaac atgtgagcaa aaggccagca aaaggccagg    4140
aaccgtaaaa aggccgcgtt gctggcgttt ttccataggc tccgcccccc tgacgagcat    4200
cacaaaaatc gacgctcaag tcagaggtgg cgaaacccga caggactata agataccag    4260 gcgtttcccc ctggaagctc cctcgtgcgc tctcctgttc cgaccctgcc gcttaccgga    4320
tacctgtccg cctttctccc ttcgggaagc gtggcgcttt ctcatagctc acgctgtagg    4380
tatctcagtt cggtgtaggt cgttcgctcc aagctgggct gtgtgcacga accccccgtt    4440
cagcccgacc gctgcgcctt atccggtaac tatcgtcttg agtccaaccc ggtaagacac    4500
gacttatcgc cactggcagc agccactggt aacaggatta gcagagcgag gtatgtaggc    4560
ggtgctacag agttcttgaa gtggtggcct aactacggct acactagaag gacagtattt    4620
```

```
ggtatctgcg ctctgctgaa gccagttacc ttcggaaaaa gagttggtag ctcttgatcc    4680
ggcaaacaaa ccaccgctgg tagcggtggt ttttttgttt gcaagcagca gattacgcgc    4740
agaaaaaaag gatctcaaga agatcctttg atctttccta cggggtctga cgctcagtgg    4800
aacgaaaact cacgttaagg gattttggtc atgagattat caaaaaggat cttcacctag    4860
atccttttaa attaaaaatg aagttttaaa tcaatctaaa gtatatatga gtaaacttgg    4920
tctgacagtt accaatgctt aatcagtgag gcacctatct cagcgatctg tctatttcgt    4980
tcatccatag ttgcctgact ccccgtcgtg tagataacta cgatacggga gggcttacca    5040
tctggcccca gtgctgcaat gataccgcga gacccacgct caccggctcc agatttatca    5100
gcaataaacc agccagccgg aagggccgag cgcagaagtg gtcctgcaac tttatccgcc    5160
tccatccagt ctattaattg ttgccgggaa gctagagtaa gtagttcgcc agttaatagt    5220
ttgcgcaacg ttgttgccat tgctgcaggc atcgtggtgt cacgctcgtc gtttggtatg    5280
gcttcattca gctccggttc ccaacgatca aggcgagtta catgatcccc catgttgtgc    5340
aaaaaagcgg ttagctcctt cggtcctccg atcgttgtca gaagtaagtt ggccgcagtg    5400
ttatcactca tggttatggc agcactgcat aattctctta ctgtcatgcc atccgtaaga    5460
tgcttttctg tgactggtga gtactcaacc aagtcattct gagaatagtg tatgcggcga    5520
ccgagttgct cttgcccggc gtcaacacgg gataataccg cgccacatag cagaacttta    5580
aaagtgctca tcattggaaa acgttcttcg gggcgaaaac tctcaaggat cttaccgctg    5640
ttgagatcca gttcgatgta acccactcgt gcacccaact gatcttcagc atcttttact    5700
ttcaccagcg tttctgggtg agcaaaaaca ggaaggcaaa atgccgcaaa aaagggaata    5760
agggcgacac ggaaatgttg aatactcata ctcttccttt ttcaatatta ttgaagcatt    5820
tatcagggtt attgtctcat gagcggatac atatttgaat gtatttagaa aaataaacaa    5880
ataggggttc cgcgcacatt tccccgaaaa gtgccacctg acgtctaaga aaccattatt    5940
atcatgacat taacctataa aaataggcgt atcacgaggc cctttcgtct tcaagaattc    6000
ataccagatc accgaaaact gtcctccaaa tgtgtccccc tcacactccc aaattcgcgg    6060
gcttctgcct cttagaccac tctaccctat tccccacact caccggagcc aaagccgcgg    6120
cccttccgtt tctttgcttt tgaaagaccc cacccgtagg tggcaagcta gcttaagtaa    6180
cgccactttg caaggcatgg aaaaatacat aactgagaat agaaaagttc agatcaaggt    6240
caggaacaaa gaaacagctg aataccaaac aggatatctg tggtaagcgg ttcctgcccc    6300
ggctcagggc caagaacaga tgagacagct gagtgatggg ccaaacagga tatctgtggt    6360
aagcagttcc tgccccggct cggggccaag aacagatggt ccccagatgc ggtccagccc    6420
tcagcagttt ctagtgaatc atcagatgtt tccaggtgc cccaaggacc tgaaaatgac    6480
cctgtacctt atttgaacta accaatcagt tcgcttctcg cttctgttcg cgcgcttccg    6540
ctctccgagc tcaataaaag agcccacaac ccctcactcg gcgcgccagt cttccgatag    6600
actgcgtcgc ccgggtaccc gtattcccaa taaagcctct tgctgtttgc atccgaatcg    6660
tggtctcgct gttccttggg agggtctcct ctgagtgatt gactaccac gacggggtc    6720 tttcatttgg gggctcgtcc gggatttgga dacccctgcc cagggaccac cgacccacca    6780
ccgggaggta agctggccag caacttatct gtgtctgtcc gattgtctag tgtctatgtt    6840
tgatgttatg cgcctgcgtc tgtactagtt agctaactag ctctgtatct ggcggacccg    6900
tggtggaact gacgagttct gaacacccgg ccgcaaccct gggagacgtc ccagggactt    6960
```

```
tgggggccgt ttttgtggcc cgacctgagg aagggagtcg atgtggaatc cgaccccgtc    7020
aggatatgtg gttctggtag gagacgagaa cctaaaacag ttcccgcctc cgtctgaatt    7080
tttgctttcg gtttggaacc gaagccgcgc gtcttgtctg ctgcagcgct gcagcatcgt    7140
tctgtgttgt ctctgtctga ctgtgtttct gtatttgtct gaaaattagg gccagactgt    7200
taccactccc ttaagtttga ccttaggtca ctggaaagat gtcgagcgga tcgctcacaa    7260
ccagtcggta gatgtcaaga agagacgttg ggttaccttc tgctctgcag aatggccaac    7320
cttttaacgtc ggatggccgc gagacggcac ctttaaccga gacctcatca cccaggttaa    7380
gatcaaggtc ttttcacctg gcccgcatgg acacccagac caggtcccct acatcgtgac    7440
ctgggaagcc ttggcttttg accccctcc ctgggtcaag ccctttgtac accctaagcc    7500
tccgcctcct cttcctccat ccgcccgtc tctccccctt gaacctcctc gttcgacccc    7560
gcctcgatcc tccctttatc cagccctcac tccttctcta ggcgccggaa ttccgatctg    7620
atcaagagac aggatgagga tcgtttcgca tgattgaaca agatggattg cacgcaggtt    7680
ctccggccgc ttgggtggag aggctattcg gctatgactg ggcacaacag acaatcggct    7740
gctctgatgc cgccgtgttc cggctgtcag cgcaggggcg cccggttctt tttgtcaaga    7800
ccgacctgtc cggtgccctg aatgaactgc aggacgaggc agcgcggcta tcgtggctgg    7860
ccacgacggg cgttccttgc gcagctgtgc tcgacgttgt cactgaagcg ggaagggact    7920
ggctgctatt gggcgaagtg ccggggcagg atctcctgtc atctcacctt gctcctgccg    7980
agaaagtatc catcatggct gatgcaatgc ggcggctgca tacgcttgat ccggctacct    8040
gcccattcga ccaccaagcg aaacatcgca tcgagcgagc acgtactcgg atggaagccg    8100
gtcttgtcga tcaggatgat ctggacgaag agcatcaggg gctcgcgcca gccgaactgt    8160
tcgccaggct caaggcgcgc atgcccgacg gcgaggatct cgtcgtgacc catggcgatg    8220
cctgcttgcc gaatatcatg gtggaaaatg gccgcttttc tggattcatc gactgtggcc    8280
ggctgggtgt ggcggaccgc tatcaggaca tagcgttggc tacccgtgat attgctgaag    8340
agcttggcgg cgaatgggct gaccgcttcc tcgtgcttta cggtatcgcc gctcccgatt    8400
cgcagcgcat cgccttctat cgccttcttg acgagttctt ctgagcggga ctctggggtt    8460
cgaaatgacc gaccaagcga cgcccaacct gccatcacga gatttcgatt ccaccgccgc    8520
cttctatgaa aggttgggct tcggaatcgt tttccgggac gccggctgga tgatcctcca    8580
gcgcggggat ctcatgctgg agttcttcgc ccaccccggg ctcgatcccc tcgcgagttg    8640
gttcagctgc tgcctgaggc tggacgacct cgcggagttc taccggcagt gcaaatccgt    8700
cggcatccag gaaaccagca gcggctatcc gcgcatccat gcccccgaac tgcaggagtg    8760
gggaggcacg atgccgcctt tggtcgaggc ggatccggcc attagccata ttattcattg    8820
gttatatagc ataaatcaat attggctatt ggccattgca tacgttgtat ccatatcata    8880
atatgtacat ttatattggc tcatgtccaa cattaccgcc atgttgacat tgattattga    8940
ctagttatta atagtaatca attacggggt cattagttca tagcccatat atggagttcc    9000
gcgttacata acttacggta aatggcccgc ctggctgacc gcccaacgac ccccgcccat    9060
tgacgtcaat aatgacgtat gttcccatag taacgccaat agggactttc cattgacgtc    9120
aatgggtgga gtatttacgg taaactgccc acttggcagt acatcaagtg tatcatatgc    9180
caagtacgcc ccctattgac gtcaatgacg gtaaatggcc cgcctggcat tatgcccagt    9240
acatgacctt atgggacttt cctacttggc agtacatcta cgtattagtc atcgctatta    9300
ccatggtgat gcggttttgg cagtacatca atgggcgtgg atagcggttt gactcacggg    9360
```

```
gatttccaag tctccacccc attgacgtca atgggagttt gttttggcac caaaatcaac    9420
gggactttcc aaaatgtcgt aacaactccg ccccattgac gcaaatgggc ggtaggcatg    9480
tacggtggga ggtctatata agcagagctc gtttagtgaa ccgtcagatc gcctggagac    9540
gccatccacg ctgttttgac ctccatagaa gacaccggga ccgatccagc ctccgcggcc    9600
ccaagcttgt tatccacc                                                  9618
```

ACTIVATABLE FUSION PROTEIN AND USE THEREOF

CROSS-REFERENCE TO RELATED APPLICATION

This application claims priority of Taiwanese Invention Patent Application No. 110104031, filed on Feb. 3, 2021.

FIELD

The present disclosure relates to an activatable fusion protein and a method for suppressing a T cell-dependent immune response.

BACKGROUND

T cells play a major role in the initiation and regulation of immune responses. For complete activation of T cells to occur, at least two distinct signaling events are required. The first signal is antigen-specific and is produced by the interaction of T-cell receptors (TCRs) expressed on T cells with specific antigens (Ag) presented in the context of major histocompatibility complex (MHC) molecules expressed on antigen-presenting cells (APCs). The second signal is a co-stimulatory signal provided by the interactions between receptors on the T cells and their ligands on the APC.

A dominant co-stimulation pathway involves the interaction between the CD80 and CD86 ligands (also referred to collectively as B7-proteins) expressed on APCs with CD28 and cytotoxic T lymphocyte-associated antigen 4 (CTLA4) expressed on T cells. Involvement of both TCRs/MHC and co-stimulatory interactions leads to T-cell activation via a number of intracellular pathways, including calcium-calcineurin and mitogen-activated protein kinase, and enhances the production of factors central to T cell proliferation and survival, such as interleukin-2 (IL-2), NF-KB, and Bcl-XL.

The CD28 receptor is a critical regulator of T cell function, making it an attractive therapeutic target for the treatment of immune mediated diseases. CTLA4 is structurally homologous to CD28 but binds to CD80 and CD86 ligands with greater avidity than to CD28. CTLA4 is a cell surface protein, having an N-terminal extracellular domain, a transmembrane domain, and a C-terminal cytoplasmic domain. CTLA4 competes with CD28 for the CD80 and CD86 ligands and thus blocks co-stimulation, and the result is a negative signal or down-regulation of the activated T-lymphocyte and the immune response.

Abatacept (Orencia®) is a CTLA4-Ig immunoadhesin consisting of the extracellular domain of human CTLA4 linked to the Fc domain of human immunoglobulin G1 (IgG1), which prevents naive T cell activation by binding to B7-proteins and blocking engagement of CD28. Abatacept has been developed for use in adult rheumatoid arthritis and juvenile idiopathic arthritis and has been indicated for reducing major clinical response, inhibiting the progression of structural damage, and improving physical function in adult patients with moderately to severely active rheumatoid arthritis. However, it has been reported that, Abatacept can systemically inhibit T cell activation and cause adverse events including headache, nausea, serious infection (e.g., urinary tract infection, nasopharyngitis, bronchitis, or pneumonia), and malignancy (Bruce S. P. et al. (2007), *Annals of Pharmacotherapy*, 41: 1153-1162; and Nash P. et al. (2013), *Arthritis care & research*, 65: 718-728).

SUMMARY

Therefore, a first object of the disclosure is to provide an activatable fusion protein that can alleviate at least one of the drawbacks of the prior art.

The activatable fusion protein includes, in an N- to C-terminal direction:
an albumin;
a matrix metalloproteinase-cleavable linker; and
an immunoadhesin which includes a cytotoxic T lymphocyte-associated antigen 4 (CTLA4) having an N-terminal extracellular domain and an IgG Fc region;
wherein the albumin is released from the activatable fusion protein in the presence of a matrix metalloproteinase that cleaves the matrix metalloproteinase-cleavable linker, so that the N-terminal extracellular domain of the CTLA4 binds to cluster of differentiation 80 (CD80) or cluster of differentiation 86 (CD86).

A second object of the disclosure is to provide a method for suppressing a T cell-dependent immune response, which can alleviate at least one of the drawbacks of the prior art.

The method includes administering to a subject in need thereof an activatable fusion protein as described above.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which.

DETAILED DESCRIPTION

Figure 1:
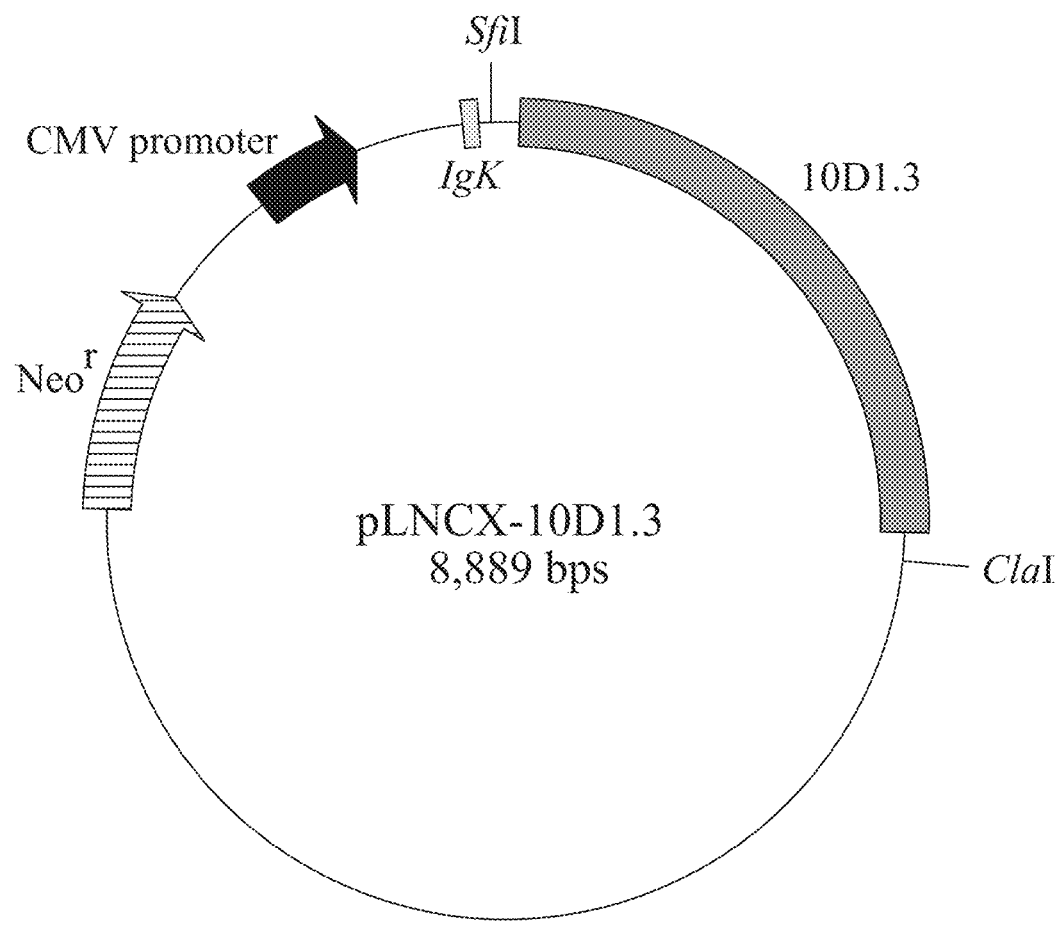
FIG. 1 shows the construct of a plasmid pLNCX-10D1.3, in which: Neo$^r$ represents a neomycin-resistance gene; SfiI and ClaI represent the restriction sites for the corresponding restriction enzymes; Igk represents a coding sequence of Igk secretion signal peptide; and 10D1.3 represents a coding sequence of antibody 10D1.3.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "gene", "cDNA", "mRNA", "oligo-nucleotide", and "polynucleotide" in use.

As used herein, the term "DNA fragment" refers to a DNA polymer, in the form of a separate segment or as a component of a larger DNA construct, which has been derived either from isolated DNA or synthesized chemically or enzymatically such as by methods disclosed elsewhere.

Unless otherwise indicated, a nucleic acid sequence, in addition to the specific sequences described herein, also covers its complementary sequence, and the conservative analogs, related naturally occurring structural variants and/or synthetic non-naturally occurring analogs thereof.

Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes deoxythymidine or an analog thereof.

The term "3'" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3'-end" and "3'-terminus", as used herein in reference to a nucleic acid molecule, refer to the end of the nucleic acid which contains a free hydroxyl group attached to the 3' carbon of the terminal pentose sugar. The terms "5'-end" and "5'-terminus", as used herein in reference to a nucleic acid molecule, refer to the end of the nucleic acid molecule which contains a free hydroxyl or phosphate group attached to the 5' carbon of the terminal pentose sugar.

As used herein, the term "transformation" can be used interchangeably with the term "transfection" when such term is used to refer to the introduction of an exogenous nucleic acid molecule into a selected host cell. According to techniques known in the art, a nucleic acid molecule (e.g., a recombinant DNA construct or a recombinant vector) can be introduced into a selected host cell by various techniques, such as calcium phosphate- or calcium chloride-mediated transfection, electroporation, microinjection, particle bombardment, liposome-mediated transfection, transfection using bacterial bacteriaphages, transduction using retroviruses or other viruses (such as vaccinia virus or baculovirus of insect cells), protoplast fusion, *Agrobacterium*-mediated transformation, or other methods.

The terms "cell", "host cell", "transformed host cell", and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

The terms "polypeptide", "peptide", and "protein" as used herein can be interchangeably used, and refer to a polymer formed of amino acid residues, wherein one or more amino acid residues are naturally occurring amino acids or artificial chemical mimics.

As used herein, the term "activatable" means that a protein exhibits a first level of binding to a binding partner when in a native or non-activated state (i.e., a first conformation), and a second level of binding to a binding partner in an activated state (i.e., a second conformation), wherein the second level of binding is greater than the first level of binding. In general, access of a binding partner to the functional protein is greater in the presence of an enzyme capable of activating the activatable linker than in the absence of such enzyme. Therefore, in the non-activated or uncleaved state, the protein is masked from target binding (i.e., the first conformation is such that the peptide mask inhibits access of the binding partner to the protein), and in the activated or cleaved state, the protein is unmasked to the binding partner.

As used herein, the term "immunoadhesin" can be used interchangeably with the terms "Fc fusion", "Ig fusion", "receptor Fc fusion", "Ig chimera", and "receptor globulin", and refer to a protein wherein one or more polypeptides is operably linked to a Fc region. An immunoadhesin combines the Fc region of an immunoglobulin with a fusion partner, which in general can be any protein or small molecule that has specificity for a target protein. Thus, immunoadhesins have two principal portions (i.e., a target binding portion and a Fc portion). The target binding portion may have specificity for virtually any target or target antigen. The Fc portion may bind to one or more Fc receptors or Fc ligands. Fusion partners may be linked to any region of a Fc region, including at the N- or C-terminus, or at some residue in-between the terminus. While virtually any protein or small molecule may be linked to Fc to generate a Fc fusion, and thus target virtually any target, immunoadhesins of the present disclosure comprise a cytotoxic T lymphocyte-associated antigen 4 (CTLA4) or a variant of CTLA4 as a fusion partner. The fusion of CTLA4 with an Ig Fc region is referred to herein as a CTLA4-Ig or CTLA4-Ig protein.

The present disclosure provides an activatable fusion protein including, in an N- to C-terminal direction:
an albumin;
a matrix metalloproteinase-cleavable linker; and
an immunoadhesin which includes a CTLA4 having an N-terminal extracellular domain and an IgG Fc region;
wherein the albumin is released from the activatable fusion protein in the presence of a matrix metalloproteinase that cleaves the matrix metalloproteinase-cleavable linker, so that the N-terminal extracellular domain of the CTLA4 binds to cluster of differentiation 80 (CD80) or cluster of differentiation 86 (CD86).

According to the present disclosure, the albumin includes an amino acid sequence that has at least 90% sequence identity to an amino acid sequence of SEQ ID NO: 2.

According to the present disclosure, the IgG Fc region may be selected from the group consisting of an IgG1 Fc region, an IgG2 Fc region, an IgG3 Fc region, an IgG4 Fc region, and combinations thereof.

According to the present disclosure, the matrix metalloproteinase is selected from the group consisting of matrix metalloproteinase 2, matrix metalloproteinase 3, matrix metalloproteinase 9, matrix metalloproteinase 13, and combinations thereof.

According to the present disclosure, the matrix metalloproteinase-cleavable linker has an amino acid sequence of CPPCPAPELLGGPA.

According to the present disclosure, the N-terminal extracellular domain includes an amino acid sequence that has at least 90% sequence identity to an amino acid sequence of SEQ ID NO: 17.

The present disclosure also provides a method for suppressing a T cell-dependent immune response, which includes administering to a subject in need thereof an activatable fusion protein as described above.

As used herein, the term "administration" or "administering" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, examples of the T cell-dependent immune response include, but are not limited to, autoimmune diseases (such as multiple sclerosis, rheumatoid arthritis, type 1 diabetes (T1D), myasthenia gravis, systemic lupus erythematosus, autoimmune hemolytic anemia, ulcerative colitis, Crohn's disease, and Sjögren's syndrome), graft rejection, graft versus host diseases (GVHD), allergic diseases (such as contact hypersensitivity, allergic rhinitis, food allergy, and asthma), T cell lymphoma, and benign lymphocytic angiitis.

According to the present disclosure, the activatable fusion protein may be prepared into a pharmaceutical composition in a dosage form suitable for, e.g., parenteral or oral administration, using technology well known to those skilled in the art. The suitable dosage form includes, but is not limited to, injections (e.g., sterile aqueous solutions or dispersions), sterile powder, tablets, troches, lozenges, capsules, dispersible powder, granule, solutions, suspensions, emulsions, syrup, elixirs, slurry, and the like.

According to the present disclosure, the pharmaceutical composition may be administered by parenteral routes selected from the group consisting of intraperitoneal injection, intrapleural injection, intramuscular injection, intravenous injection, intraarterial injection, intraarticular injection, intrasynovial injection, intrathecal injection, intracranial injection and sublingual administration.

The pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The dosage and the frequency of administration of the pharmaceutical composition may vary depending on the following factors: the severity of the disease to be treated, the route of administration, and the weight, age, physical condition and response of the subject to be treated. The daily dosage of the pharmaceutical composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials:
1. The following experimental materials were purchased from New England Biolabs, Inc.: restriction enzyme SfiI (Cat. No. R0123S), restriction enzyme ClaI (Cat. No. R0197S), restriction enzyme HindIII (Cat. No. R3104S), Phusion® High-Fidelity DNA polymerase (Cat. No. M0530S), and Quick Ligation™ Kit (Cat. No. M2200S).
2. The following experimental materials were purchased from Geneaid: GenepHlow™ Gel/PCR Kit (Cat. No. DFH100) and Presto™ Mini Plasmid Kit (Cat. No. PDH100).
3. The primers for polymerase chain reaction (PCR) as used in the examples were synthesized by Genomics Inc.
4. Vectors used in the following examples are described as follows:
   (1) Plasmid pDNR-LIB-ALB (6,031 bps) was prepared by GenDiscovey Biotechnology Inc. Plasmid pDNR-LIB-ALB carries an ALB gene (SEQ ID NO: 1).
   (2) Plasmid pUC57-linker-CTLA4E-IgG1H (3,253 bps) was prepared by Genomics Inc. Plasmid pUC57-linker-CTLA4E-IgG1H carries a linker-CTLA4E-IgG1H DNA fragment (SEQ ID NO: 3) encoding a fusion protein that includes a matrix metalloproteinase-cleavable linker, an N-terminal extracellular domain of cytotoxic T lymphocyte-associated antigen 4 (CTLA4), a hinge region of IgG1, and a partial CH2 domain of IgG1.
   (3) Plasmid pD5-IgG1Fc (4,393 bps) was kindly provided by Professor Kuang-Wen Liao (National Yang Ming Chiao Tung University, Taiwan). Plasmid pD5-IgG1Fc carries an IgG1CH2-CH3 DNA fragment (SEQ ID NO: 4) encoding a fusion protein that includes a partial CH2 domain of IgG1 and complete CH3 domains of IgG1.
   (4) Plasmid pLNCX-10D1.3 (8,889 bps, see SEQ ID NO: 5 and FIG. 1) was kindly provided by Professor Tian-Lu Cheng (Kaohsiung Medical University, Taiwan). Plasmid pLNCX-10D1.3 carries a cytomegalovirus (CMV) promoter, a coding sequence of Igκ secretion signal peptide (SEQ ID NO: 6), a coding sequence of antibody 10D1.3, a neomycin-resistance gene (Neo$^r$), and restriction sites for SfiI and ClaI.
   (5) Plasmid pLNCX-CD80 (7494 bps) was prepared by GenDiscovey Biotechnology Inc. Plasmid pLNCX-CD80 carries a CMV promoter, a coding sequence of cluster of differentiation 80 (CD80), and a neomycin-resistance gene (Neo$^r$), General Procedures:
1. The experimental procedures related to DNA cloning as employed in the examples of the present disclosure, such as extraction of genomic DNA, DNA cleavage reactions by restriction enzymes, agarose gel electrophoresis, PCR, DNA ligation with T4 DNA ligase, sodium dodecyl sulfate-polyacrylamide gel electrophoresis (SDS-PAGE), Western blotting, plasmid transformation, etc., were performed by virtue of techniques well known to those skilled in the art or in accordance with the manufacturer's instructions.

2. Preparation of Competent *E. coli* Cells:

*Escherichia coli* DH5a (Yeastern Biotech Co., Ltd., Cat. No. FYE607-10VL) was inoculated into LB broth and cultivated at 37° C. with shaking (225 rpm) for 14 hours. Thereafter, 4 mL of the cell culture thus obtained was inoculated into 100 mL of fresh LB broth and cultivated at 37° C. with shaking (225 rpm). Upon reaching a cell density of about 0.2~0.4 ($OD_{600}$), the resultant culture was transferred into a sterile centrifuge tube, followed by centrifugation (4° C., 2,000×g, 15 minutes). After removal of the supernatant, 1 mL of an ice cold $CaCl_2$) solution (0.1 M) was added into the centrifuge tube to thoroughly suspend the bacterial cells, followed by adding 13 mL of an ice cold $CaCl_2$) solution (0.1 M), so as to obtain a bacterial cell suspension. The resultant bacterial cell suspension was allowed to stand on ice for 15 minutes, followed by centrifugation (4° C., 2,000×g, 15 minutes). After removal of the supernatant, 1 mL of an ice cold $CaCl_2$) solution (0.1 M, containing 20% glycerol) was added into the centrifuge tube to thoroughly suspend the bacterial cells, followed by adding 9 mL of an ice cold $CaCl_2$ solution (0.1 M, containing 20% glycerol), so that a suspension of $CaCl_2$-treated competent *E. coli* cells was obtained. The competent *E. coli* cell suspension was then aliquoted into microcentrifuge tubes (300 μL per tube) and stored at −80° C. until use.

3. Source and Cultivation of Cell Lines:

Human embryonic kidney cell line HEK-293, human embryonic kidney cell line 293T, human acute T-cell leukemia cell line Jurkat, and human B-lymphocyte cell line Raji were all purchased from American Type Culture Collection (ATCC, Manassas, Va., USA).

Each of the cell lines was cultivated using a corresponding medium shown in Table 1 and a 6-cm Petri dish in an incubator (37° C. and 5% $CO_2$). Medium change was performed every two days. Cell passage was performed when the cultured cells reached 70% of confluence.

TABLE 1

| Cell line | Medium |
| --- | --- |
| HEK-293 (ATCC ® CRL-1573 ™) 293T (ATCC ® CRL-3216 ™) | Dulbecco's Modified Eagle's Medium (DMEM)(MyClone) supplemented with 10% fetal bovine serum (FBS)(MyClone) and 50 μg/mL gentamicin (Cyrusbio Inc) |
| Jurkat (ATCC ® TIB-152 ™) Raji (ATCC ® CCL-86 ™) | RPMI 1640 medium (Gibco) supplemented with 10% FBS 100 U/mL penicillin, and 100 μg/mL streptomycin (Gibco) |

Example 1. Construction of Recombinant Plasmid pLNCX-ALB-Linker-CTLA4-Ig

A. Cloning of ALB Gene, Linker-CTLA4E-IgG1H DNA Fragment, and IgG1CH2-CH3 DNA Fragment A respective one of the plasmid pDNR-LIB-ALB, plasmid pUC57-linker-CTLA4E-IgG1H, and plasmid pD5-IgG1Fc described in section 4 of "General Experimental Materials" was used as a template and subjected to a PCR process using a corresponding one of the primer pairs 1-3 described in Table 2, respectively. The PCR conditions are shown in Tables 3-4.

TABLE 2

| Primer pair | Primer | Nucleotide sequence (5' → 3') | Target DNA fragment | Size of PCR product (bp) |
| --- | --- | --- | --- | --- |
| 1 | Forward primer F1 | SfiI cgtaggcccagccggccgatgcacacaa gagtgaggttg (SEQ ID NO: 7) | ALB gene (SEQ ID NO: 1) | 1,783 |
|   | Reverse primer R1 | cacggtgggcataagcctaaggcagctt gac (SEQ ID NO: 8) |   |   |
| 2 | Forward primer F2 | cttaggcttatgcccaccgtg (SEQ ID NO: 9) | Linker-CTLA4E-IgG1H DNA fragment (SEQ ID NO: 3) | 543 |
|   | Reverse primer R2 | gagatcatgagggtgtccttg (SEQ ID NO: 10) |   |   |
| 3 | Forward primer F3 | caaggacaccctcatgatctc (SEQ ID NO: 11) | IgG1CH2-CH3 DNA fragment (SEQ ID NO: 4) | 633 |
|   | Reverse primer R3 | ClaI gtcatatcgattcaatggtgatggtga tgatgtttacccggagacagggagag (SEQ ID NO: 12) |   |   |

Note:
The underlined nucleotides represent the recognition site of the restriction enzyme indicated thereabove, and the nucleotides shown in the boxes represent the 6xHis-tag.

TABLE 3

| Contents | Volume (μL) |
| --- | --- |
| Plasmid DNA (10 ng/μL) | 1 |
| Forward primer (20 μm) | 1.6 |
| Reverse primer (20 μm) | 1.6 |
| dNTPs (10 mM) | 0.5 |
| Phusion ® High-Fidelity DNA polymerase (0.5 U/μL) | 0.25 |
| 5× Phusion HF buffer | 5 |
| Nuclease-free water | 15.05 |

TABLE 4

| Primer pair | Operation conditions |
|---|---|
| 1 | Denaturation at 98° C. for 30 seconds, followed by |
| 2 | 30 cycles of the following reactions: denaturation at 98° C. for 10 seconds, primer annealing at 61° C. for 20 seconds, and elongation at 72° C. for 23 seconds; and finally extra extension at 72° C. for 5 minutes. |
| 3 | Denaturation at 98° C. for 30 seconds, followed by 30 cycles of the following reactions: denaturation at 98° C. for 10 seconds, primer annealing at 67° C. for 20 seconds, and elongation at 72° C. for 23 seconds; and finally extra extension at 72° C. for 5 minutes. |

Consequently, a PCR product A1 containing an ALB gene (1,783 bps), a PCR product A2 containing a linker-CTLA4E-IgG1H DNA fragment (543 bps), and a PCR product A3 containing an IgG1CH2-CH3 DNA fragment (633 bps) were obtained.

The resultant PCR products were subjected to a 1% agarose gel electrophoresis analysis for molecular weight verification, followed by recovery and purification using the GenepHlow™ Gel/PCR Kit.

B. Synthesis of ALB-Linker-CTLA4-Ig DNA Fragment

A respective one of the PCR product A1 and PCR product A2 obtained in section A of this example was dissolved in nuclease-free water, followed by conducting overlapping PCR using the forward primer F1 and reverse primer R2 described in Table 2. The overlapping PCR conditions are shown in Table 5.

TABLE 5

| Contents | Volume (μL) |
|---|---|
| PCR product A1 | 1 |
| PCR product A2 | 1 |
| Forward primer F1 (20 μm) | 1.6 |
| Reverse primer R2 (20 μm) | 1.6 |
| dNTP (10 mM) | 0.5 |
| Phusion ® High-Fidelity DNA polymerase (0.5 U/μL) | 0.25 |
| 5× Phusion HF buffer | 5 |
| Nuclease-free water | 15.05 |
| Operation conditions: denaturation at 98° C. for 30 seconds, followed by 30 cycles of the following reactions: denaturation at 98° C. for 10 seconds, primer annealing at 67° C. for 20 seconds, and elongation at 72° C. for 23 seconds; and finally extra extension at 72° C. for 5 minutes. | |

Consequently, a PCR product A4 having a size of about 2,305 bps (see SEQ ID NO: 13) was obtained. The resultant PCR product A4 was subjected to a 1% agarose gel electrophoresis analysis for molecular weight verification, followed by recovery and purification using the GenepHlow™ Gel/PCR Kit.

Thereafter, a respective one of the PCR product A3 obtained in section A of this example and PCR product A4 obtained above was dissolved in nuclease-free water, followed by conducting overlapping PCR using the forward primer F1 and reverse primer R3 described in Table 2. The overlapping PCR conditions are shown in Table 6.

TABLE 6

| Contents | Volume (μL) |
|---|---|
| PCR product A3 | 1 |
| PCR product A4 | 1 |
| Forward primer F1 (20 μm) | 1.6 |
| Reverse primer R3 (20 μm) | 1.6 |
| dNTPs (10 mM) | 0.5 |
| Phusion ® High-Fidelity DNA polymerase (0.5 U/μL) | 0.25 |
| 5× Phusion HF buffer | 5 |
| Nuclease-free water | 15.05 |
| Operation conditions: denaturation at 98° C. for 30 seconds, followed by 30 cycle of the following reactions: denaturation at 98° C. for 10 seconds, primer annealing at 72° C. for 20 seconds, and elongation at 72° C. for 23 seconds; and finally extra extension at 72° C. for 5 minutes. | |

Consequently, a PCR product A5 containing an ALB-linker-CTLA4-Ig DNA fragment (2,917 bps, see SEQ ID NO: 14) was obtained. The resultant PCR product A5 was subjected to a 1% agarose gel electrophoresis analysis for molecular weight verification, followed by recovery and purification using the GenepHlow™ Gel/PCR Kit.

Regarding the ALB-linker-CTLA4-Ig DNA fragment, which encodes an activatable fusion protein having an amino acid sequence as shown in SEQ ID NO: 15, wherein the $1^{st}$-$585^{th}$ amino acid residues from the N-terminus constitute an albumin (SEQ ID NO: 2), the $586^{th}$-$599^{th}$ amino acid residues from the N-terminus constitute a matrix metalloproteinase-cleavable linker (SEQ ID NO: 16), the $600^{th}$-$724^{th}$ amino acid residues from the N-terminus constitute an N-terminal extracellular domain of CTLA4 (SEQ ID NO: 17), and the $725^{th}$-$956^{th}$ amino acid residues from the N-terminus constitute an IgG1 Fc region (SEQ ID NO: 18).

C. Construction of Recombinant Plasmid pLNCX-ALB-Linker-CTLA4-Ig

Figure 2:
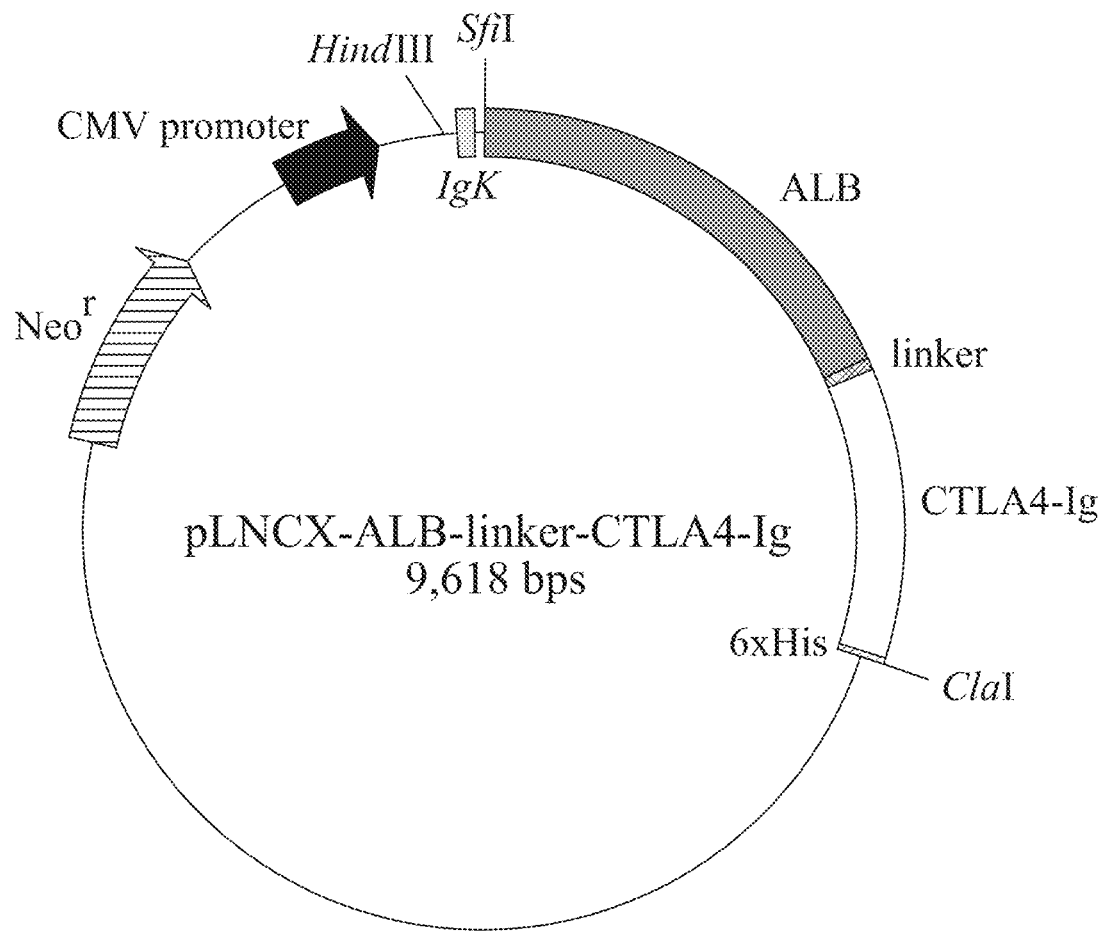
FIG. 2 shows the construct of a recombinant plasmid pLNCX-ALB-linker-CTLA4-Ig, in which Neo$^r$ represents a neomycin-resistance gene; SfiI, ClaI, and HindIII represent the restriction sites for the corresponding restriction enzymes; ALB represents a coding sequence of albumin; linker represents a coding sequence of a matrix metalloproteinase-cleavable linker; CTLA4-Ig represents a coding sequence of a CTLA4-Ig immunoadhesin; and 6×His represents hexahistidine tag.

A DNA fragment having a size of 6,710 bps (i.e., a carrier DNA) was excised from Plasmid pLNCX-10D1.3 using restriction enzymes SfiI/ClaI. In addition, a DNA fragment having a size of 2,908 bps and possessing the ALB-linker-CTLA4-Ig DNA fragment (i.e., an insert DNA) was excised from the PCR product A5 obtained in section B of this example using restriction enzymes SfiI/ClaI. Subsequently, the carrier DNA and the insert DNA were subjected to ligation in a molar ratio of 1 to 3 using the Quick Ligation™ Kit, thereby forming a recombinant plasmid pLNCX-ALB-linker-CTLA4-Ig having a nucleotide sequence as shown in SEQ ID NO: 19 (9,618 bps, see FIG. 2).

Subsequently, a microcentrifuge tube containing a competent E. coli cell suspension as prepared in section 2 of "General Procedures" was removed from −80° C.-storage and allowed to stand on ice for at least 15 minutes, so that the competent E. coli cell suspension stored therein was thawed. 100 μL of the thawed competent E. coli cell suspension was then evenly admixed with 5 μL of the recombinant plasmid pLNCX-ALB-linker-CTLA4-Ig, followed by standing on ice for 30 minutes.

The resulting mixture was then placed in a 42° C. water bath for 30 seconds, followed by standing on ice for 5 minutes. After evenly admixing with 900 μL SOC medium (Cyrusbio Inc), the resulting mixture was cultivated at 37° C. with shaking (225 rpm) for 1 hour. The bacterial culture thus obtained was plated on a LB agar plate containing 100 μg/mL ampicillin and cultivated at 37° C. for 14 hours.

The resultant culture was harvested and the recombinant plasmid pLNCX-ALB-linker-CTLA4-Ig contained therein was extracted using the Presto™ Mini Plasmid Kit, followed by cleavage using restriction enzymes HindIII/ClaI. The resultant cleavage products were subjected to agarose gel electrophoresis, so as to verify the molecular weight of the recombinant plasmid pLNCX-ALB-linker-CTLA4-Ig. The verified recombinant plasmid pLNCX-ALB-linker-CTLA4-Ig was subjected to a sequencing analysis conducted by Genomics Inc.

Example 2. Production of Fusion Protein ALB-Linker-CTLA4-Ig

A. Transfection of 293T Cells with Recombinant Plasmid pLNCX-ALB-Linker-CTLA4-Ig 10 μg of the recombinant plasmid pLNCX-ALB-linker-CTLA4-Ig obtained in Example 1, 1 mL of 0.3 M $CaCl_2$), and 1 mL of 2×HEPES buffered saline (HBS) were mixed, so as obtain a transfection mixture.

293T cells were incubated in a 10-cm petri dish containing DMEM ($3.5 \times 10^6$ cells/5 mL of DMEM), followed by cultivation in an incubator (37° C., 5% $CO_2$). After cell attachment, the liquid in the petri dish was removed, and the transfection mixture was subsequently added, followed by cultivation for 6 hours. Afterwards, 10 mL of DMEM supplemented with 10% FBS was added to the petri dish, followed by cultivation for 24 hours. After removal of the liquid, 15 mL of DMEM supplemented with 10% FBS was added to the petri dish, followed by cultivation for 24 hours and subsequent collection of the liquid culture. This step was repeated thrice, so as to obtain 60 mL of the liquid culture.

B. First Purification of Fusion Protein ALB-Linker-CTLA4-Ig

The liquid culture obtained in section A of this example was subjected to centrifugation at 1,000×g for 5 minutes to obtain a supernatant, and the supernatant was subsequently added with 1% tween-20 and 30 mM imidazole, so as to obtain a protein sample. The protein sample was then subjected to an immobilized metal ion affinity chromatography (IMAC) analysis using HisTrap™ HP column (Cat. No. 17-5248-02, GE healthcare) in accordance with the manufacturer's instructions.

Briefly, the protein sample was applied to a HisTrap™ HP column at a flow rate of 2 mL/min. Thereafter, Tris binding buffer, Tris IEX buffer, Tris glycerol buffer, and Tris DF buffer (these four buffers were all purchased from Cyrusbio Inc) were used to wash out the unbound protein in sequence, and then the bound proteins were eluted with an eluent (Cyrusbio Inc). Each fraction obtained consisted of 6 mL of an eluate. Afterwards, the eluate of each fraction was collected and then subjected to dialysis using a dialysis membrane having a molecular weight cut-off of 10 kDa and Tris-buffered saline (TBS), so as to obtain a first purified product.

Subsequently, 4 μL of the first purified product was evenly mixed with 6 μL of deionized water and 3.5 μL of a 4× sample buffer, followed by heating in a boiling water bath for 5 minutes. The resultant protein sample was allowed to cool down to room temperature, and was then subjected to SDS-PAGE and Western blot analyses. The apparatus and chemicals used are described as follows:

(1) A two-layered polyacrylamide gel consisting of a 10% SDS-PAGE separating gel and a 4% SDS-PAGE stacking gel on top of said separating gel and an electrophoresis system (Bio-Rad Inc) were used for the SDS-PAGE analysis.

(2) Protein transfer was conducted using a wet tank transfer (Bio-Rad Inc) and a nitrocellulose membrane (Pall Corporation, Cat. No. T50036).

(3) A HRP-conjugated anti-human IgG Fcγ antibody (Jackson ImmunoResearch Inc., Cat. No. 109-035-098) (diluted 20,000-fold with TBST containing 0.5% skim milk) was used for Western blot.

(4) Chemiluminescence staining was performed using an enhanced chemiluminescence (ECL) detection kit (GE Life Sciences, Cat. No. PRN2106) and a luminescence imaging system (Hansor luminescence image system, model: G595).

Figure 3:
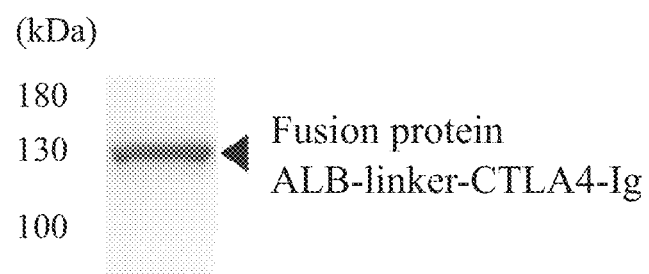
FIG. 3 is a Western blot showing expression of a fusion protein ALB-linker-CTLA4-Ig from the 293T cells transfected with the recombinant plasmid pLNCX-ALB-linker-CTLA4-Ig.

Referring to FIG. 3, the fusion protein ALB-linker-CTLA4-Ig (130 kDa) was detected by HRP-conjugated anti-human IgG $Fc_{5\mu}$ antibody, indicating that the 293T cells transfected with the recombinant plasmid pLNCX-ALB-linker-CTLA4-Ig can effectively express the fusion protein ALB-linker-CTLA4-Ig.

C. Second Purification of Fusion Protein ALB-Linker-CTLA4-Ig

3920 μL of the first purified product obtained in section B of this example, 80 μL of 500 mM EDTA, and 4000 μL of 20 mM Tris-HCl buffer were mixed, followed by filtration. The filtrate thus obtained was subjected to anion exchange chromatography using HiTrap® Q Fast Flow (GE Healthcare, Cat. No. 17-5156-01). The operation conditions used are described as follows: a flow rate of 2 mL/min; a wash buffer which was 20 mM Tris-HCl buffer; and an elution buffer which was a 2 M NaCl solution, and a gradient elution ranging from 2% to 25%. Each fraction obtained consisted of 5 mL of an eluate. Afterwards, the eluate of each fraction was collected and then subjected to dialysis using a dialysis membrane having a molecular weight cut-off of 10 kDa and TBS, so as to obtain a purified fusion protein ALB-linker-CTLA4-Ig. The purified fusion protein ALB-linker-CTLA4-Ig was then subjected to SDS-PAGE analysis described in section B of this example, followed by Coomassie blue staining.

The experimental results reveal that the purity value of the purified fusion protein ALB-linker-CTLA4-Ig is greater than 95%.

Example 3. Evaluation for the Effect of Fusion Protein ALB-Linker-CTLA4-Ig According to this Disclosure on Immune Regulation A. Preparation of Mixture Containing CTLA4-Ig 64 μg of the purified fusion protein ALB-linker-CTLA4-Ig obtained in Example 2, 63.4 μL of 5 mg/mL collagenase type IV (Sigma-Aldrich, Cat. No. C5138) (which had the activities of matrix metalloproteinase 2 (MMP2) and MMP9), 320.7 μL of 0.1% bovine serum albumin (BSA), and 320.7 μL of 1×TCNB buffer (containing 0.5% Brij-35, 0.1 M $CaCl_2$, 1.5 M NaCl, and 0.5 M Tris, pH 7.5) were mixed, followed by conducting enzymatic digestion at 30° C. for 1 hour. Afterwards, the resultant mixture was subjected to IMAC analysis and dialysis according to the method described in section B of Example 2, so as to obtain a mixture containing CTLA4-Ig.

B. Preparation of CD80-Expressing HEK-293 Cells

The plasmid pLNCX-CD80 was transfected into competent HEK-293 cells using TransIT X2@ Dynamic Delivery system (Mirus Bio Inc., Cat. No. MIR6000) according to the manufacturer's instructions. Afterward, the thus obtained CD80-expressing HEK-293 cells were subjected to flow cytometry analysis using PE anti-human CD80 antibody (BioLegend, Inc., Cat. No. 305207), so as to confirm that CD80 was successfully expressed on the HEK-293 cells.

C. Analysis of CD80-Binding Capacity

The purified fusion protein ALB-linker-CTLA4-Ig obtained in Example 2, the mixture containing CTLA4-Ig obtained in section A of this example, and a commercially available CTLA4-Ig (BioLegend Inc., Cat. No. 591902) were each subjected to serial dilution with phosphate-buffered saline (PBS), so as to obtain three test solutions having different concentrations ($10^{-4}$ to $10^{4}$ nM).

A respective well of a 96-well culture plate was added with 50 μL of 100 μg/mL poly-lysine solution (Sigma-Aldrich, Cat. No. P6282-5MG), followed by incubation at room temperature for 5 minutes. Subsequently, the liquid in each well was removed, followed by air drying for 2 hours. Afterwards, the CD80-expressing HEK-293 cells obtained in section B of this example were divided into 3 groups, including one comparative group and two experimental groups (i.e., experimental groups 1 to 2). Each group of the CD80-expressing HEK-293 cells was incubated in a respective well of the 96-well culture plate at $1\times10^{5}$ cells/well, followed by cultivation in an incubator (37° C., 5% $CO_2$) for 14 hours. Thereafter, the liquid in each well was removed, and the cultured cells were fixed with a 4% paraformaldehyde solution (in PBS) at room temperature for 1 hour.

After removal of the liquid, the cell culture in each well was washed with PBS with Tween 20 (PBST) (99.5% PBS, 0.05% Tween-20) thrice, followed by adding 200 μL of a blocking solution containing 5% skim milk in PBST. After incubation at room temperature for 1 hour, the liquid in each well was removed, followed by washing with 1×PBST thrice. Subsequently, the cell culture of the comparative group was treated with 50 μL of the test solution containing the commercially available CTLA4-Ig, the cell culture of the experimental group 1 was treated with 50 μL of the test solution containing the purified fusion protein ALB-linker-CTLA4-Ig, and the cell culture of the experimental group 2 was treated with 50 μL of the test solution containing the mixture containing CTLA4-Ig. Each group was cultivated at room temperature for 1 hour. The liquid in each well was removed, followed by washing with 1×PBST thrice. Thereafter, 100 μL of HRP-conjugated anti-human IgG Fcγ antibody (diluted 10,000-fold with PBST containing 0.5% skim milk) was added to each well, followed by incubation at room temperature for 1 hour. The liquid in each well was removed, followed by washing with 1×PBST thrice. Afterwards, 100 μL of TMB peroxidase substrate (eBioscience, Cat. No. 00-4201-56) was added to each well, followed by incubation at room temperature for 15 minutes. The respective resultant cell culture was added with 100 μL of 1M $H_3PO_4$, followed by subjecting the mixture thus obtained to determination of absorbance at a wavelength of 450 nm ($OD_{450}$) by a SpectraMax 190 Microplate reader (Molecular Devices). The 50% effective concentration ($EC_{50}$) was determined using GraphPad Prism software (GraphPad Software, San Diego, CA).

As shown in Table 7 below, the $EC_{50}$ values determined in the experimental group 2 and comparative group were significantly lower than that determined in the experimental group 1, indicating that: when the fusion protein ALB-linker-CTLA4-Ig is in an uncleaved state (i.e., inactivated state), the albumin retains the ability to effectively mask the N-terminal extracellular domain of the CTLA4 and hence can inhibit binding of the N-terminal extracellular domain to CD80; and when the albumin is released from the fusion protein ALB-linker-CTLA4-Ig by the action of MMP2 or MMP9 on the linker of the fusion protein ALB-linker-CTLA4-Ig, the N-terminal extracellular domain of the CTLA4 can bind to CD80.

TABLE 7

| Group | $EC_{50}$ value |
|---|---|
| Experimental group 1 | >4 |
| Experimental group 2 | 0.022 |
| Comparative group | 0.016 |

D. Analysis of Immunosuppressive Activity

Raji cells were divided into 3 groups, including one comparative group and two experimental groups (i.e., experimental groups 1 to 2). Each group of the Raji cells was incubated in a respective well of a 96-well culture plate at $3.2\times10^{4}$ cells/well, followed by treatment with a respective one of the three test solutions having different concentrations (i.e., 0.032 nM, 0.081 nM, 0.204 nM, 0.512 nM, 1.28 nM, 3.2 nM, 8 nM, and 20 nM) obtained in section C of this example as follows. The cell culture of the comparative group was treated with 240 μL of the test solution containing the commercially available CTLA4-Ig, the cell culture of the experimental group 1 was treated with 240 μL of the test solution containing the purified fusion protein ALB-linker-CTLA4-Ig, and the cell culture of the experimental group 2 was treated with 240 μL of the test solution containing the mixture containing CTLA4-Ig. Afterwards, each group was cultivated at 37° C. for 15 minutes.

In addition, 10.395 mL of Jurkat cells ($1\times10^{6}$ cells/mL) and 105 μL of 5000 ng/mL anti-human CD3 antibody (BioLegend, Inc., Cat. No. 317303) were added into a microcentrifuge tube, followed by incubation at 37° C. for 15 minutes. Subsequently, 100 μL of the resultant cell culture was added to each of the cell cultures of the experimental groups 1 to 2 and comparative group, followed by cultivation in an incubator (37° C., 5% $CO_2$) for 24 hours. Thereafter, each of the cell cultures was collected, and the interleukin-2 (IL-2) level of each group was determined using Human IL-2 ELISA MAX™ Standard kit (BioLegend, Inc., Cat. No. 431801) according to the manufacturer's instructions.

Figure 4:
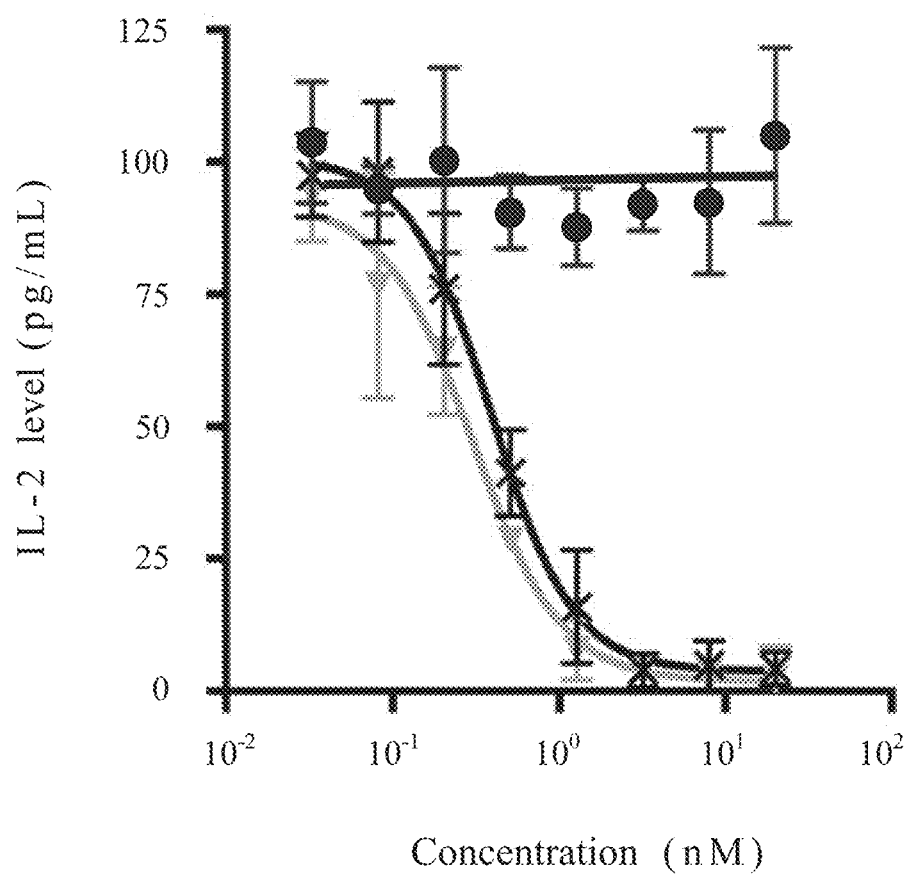
FIG. 4 shows the interleukin-2 (IL-2) level of each group described in section D of Example 3, infra.

Referring to FIG. 4, the IL-2 levels determined in the experimental group 2 and comparative group were significantly lower than that determined in the experimental group 1, indicating that when the fusion protein ALB-linker-CTLA4-Ig is in an activated state (i.e., the albumin is released from the fusion protein ALB-linker-CTLA4-Ig), it has an ability to bind CD80, and hence can inhibit or suppress the T cell-dependent immune response.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An activatable fusion protein comprising, in an N- to C-terminal direction:
- an albumin;
- a matrix metalloproteinase-cleavable linker having the amino acid sequence of SEQ ID NO: 16; and
- an immunoadhesin comprising the extracellular domain of a cytotoxic T lymphocyte-associated antigen 4 (CTLA4) and an IgG Fc region, the extracellular domain having the amino acid sequence of SEQ ID NO: 17;
- wherein the albumin is released from the activatable fusion protein in the presence of a matrix metalloproteinase that cleaves the matrix metalloproteinase-cleavable linker, so that the extracellular domain of the CTLA4 binds to cluster differentiation 80 (CD80) or cluster of differentiation 86 (CD86).

2. The activatable fusion protein according to claim 1, wherein the albumin comprises an amino acid sequence that has at least 90% sequence identity to the amino acid sequence of SEQ ID NO: 2.

3. A method for treating an inflammatory and/or autoimmune disease, comprising administering to a subject in need thereof the activatable fusion protein according claim 1.

4. The method according to claim 3, wherein the activatable fusion protein is in a dosage form for parenteral administration.

* * * * *